(12) United States Patent
Jasper

(10) Patent No.: US 8,367,414 B2
(45) Date of Patent: Feb. 5, 2013

(54) TRACING PROCESSES BETWEEN PRECURSORS AND PRODUCTS BY UTILIZING ISOTOPIC RELATIONSHIPS

(76) Inventor: John P. Jasper, Niantic, CT (US)

( * ) Notice: Subject to any disclaimer, the term of this patent is extended or adjusted under 35 U.S.C. 154(b) by 1559 days.

(21) Appl. No.: 11/807,752

(22) Filed: May 30, 2007

(65) Prior Publication Data

US 2012/0123582 A1 May 17, 2012

Related U.S. Application Data

(60) Provisional application No. 60/803,505, filed on May 30, 2006, provisional application No. 60/897,623, filed on Jan. 26, 2007.

(51) Int. Cl.
*G01N 37/00* (2006.01)
(52) U.S. Cl. ............... 436/56; 436/2; 436/91; 436/106; 436/127; 436/139; 436/145; 436/173
(58) Field of Classification Search .......... 436/2, 55–56, 436/91, 106, 127, 139, 145, 173
See application file for complete search history.

(56) References Cited

U.S. PATENT DOCUMENTS

| | | | |
|---|---|---|---|
| 3,959,630 A | 5/1976 | Hogberg | |
| 4,742,340 A | 5/1988 | Nowik | |
| 5,012,052 A | 4/1991 | Hayes | |
| 5,314,827 A | 5/1994 | Schmidt et al. | |
| 5,424,539 A | 6/1995 | Brandt et al. | |
| 5,432,058 A | 7/1995 | Lange et al. | |
| 5,474,937 A | 12/1995 | Anderson, II | |
| 5,677,187 A | 10/1997 | Anderson, II | |
| 5,760,394 A | 6/1998 | Welle | |
| 5,830,763 A | 11/1998 | Junk et al. | |
| 5,846,514 A | 12/1998 | Foster et al. | |
| 6,057,542 A | 5/2000 | Meijer et al. | |
| 6,815,213 B1 | 11/2004 | Martin et al. | |
| 2006/0031030 A1 | 2/2006 | Bennett et al. | |

FOREIGN PATENT DOCUMENTS

WO    WO 00/71966    11/2000

OTHER PUBLICATIONS

Jasper, J. P., Rapid Communications in Mass Spectrometry 2001, 15, 1554-1557.*
Phillips, S. A. et al, Science & Justice 2003, 43, 153-160.*
Jasper, J. P. et al, Journal of Pharmaceutical and Biomedical Analysis 2004, 35, 21-30.*
Jasper, J. P. et al, Pharmaceutical Technology 2004, 28, pp. 60,62,64,66-67.*
Wokovich, A. M. et al, Journal of Pharmaceutical and Biomedical Analysis 2005, 338, 781-784.*
Stanimirova, I. et al, Analytica Chimica Acta 2005, 552, 1-12.*
Martin G. et al, Flavour and Fragrance Journal 1993, 8, 97-107.*
Mas, F. et al, Forensic Science International 1995, 71, 225-231.*
Martin, G.J., "Multisite and Multicomponent Approach for the Stable Isotope Analysis of Aromas and Essential Oils" in Fruit Flavors, ACS Symposium Series, vol. 596, Chapter 8, 1995, 79-93.*
Abramson, F. P. et al, Analytical Chemistry 1996, 68, 1971-1972.*
Parker, I. G. et al, Food Chemistry 1998, 63, 423-428.*
Zhang, B.-L. et al, Journal of Agriculture and Food Chemistry 1998, 46, 1374-1380.*
Culp, R. A. et al, "Cabon Isotope Composition of Selected Flavoring Compounds for the Determination of Natural Origin by Gas Chromatography/Isotope Ratio Mass Spectrometer" in Flavor Analysis, ACS Symposium Series, vol. 705. Chapter 23, 1998, 260-287.*
Lorant, F. et al, Energy & Fuels 2000, 14, 1143-1155.*
Cramer, B. et al, Energy & Fuels 2001, 15, 517-532.*
Zhang, B.-L. et al, Journal of Agriculture and Food Chemistry 2002, 50, 1574-1580.*
Wilcke, W. et al, Environmental Science and Technology 2002, 36, 3530-3535.*
Bensaid, F. F. et al, Journal of Agriculture and Food Chemistry 2002, 50, 6271-6275.*
Schmidt, H.-L. et al, Phytochemistry Reviews 2003, 2, 61-85.*
Fugel, R. et al, Food Chemistry 2004, 87, 141-150.*
Martin, G. J. et al, Phytochemistry 2004, 65, 2815-2831.*
Camin, F. et al, Journal of Agriculture and Food Chemistry 2004, 52, 6592-6601.*
Tenailleau, E. J. et al, Journal of Agriculture and Food Chemistry 2004, 52, 7782-7787.*
Zwank, L. et al, Environmental Science and Technology 2005, 39, 1018-1029.*
Wokovich, A. M. et al, Journal of Pharmaceutical and Biomedical Analysis 2005, 38, 781-784.*
E. Wada et al., 15N Abundance in Nitrogen of Naturally Occuring Substances and Global Assessment of Denitrification From Isotopic Viewpoint, Geochemical Journal, vol. 9, pp. 139-148, 1975.
W.A. Brand, High Precision Isotope Ration Monitoring Techniques in Mass Spectrometry, Journal of Mass Spectrometry, vol. 31, pp. 225-235, 1996.
J. Thomas Brenna et al., High-Precision Countinuous-Flow Isotope Ratio Mass Spectrometry, Mass Spectroscopy Reviews, vol. 16, pp. 227-258, 1997.
Jamin, E., Naulet, N., Martin, G.J., Multi-Element and Multi-Site Isotopic Analysis of Nicotine From Tobacco Leaves; Plant, Cell and Environment (1997) 20, pp. 589-599.
J.P. Jasper et al., A Preliminary Multi-Stable-Isotopic Evaluation of Three Synthetic Pathways of Topiramate, Journal of Pharmaceutical and Biomedical Analysis 2005 (2005), 39, 65-75.
Peter Bommer, et al., Determination of the Origin of Drugs by Measuring Natural Isotope Contents: D/H and 13C/12CD Ratios of Some Diazepam Samples; Journal of Natural Research, 31, c. 111-114 (1976). J.P. Jasper, L.E. Weaner, B.J. Duffy; A Preliminary Multi-Stable Isotopic Evaluation of Three Synthetic Pathways of Topiramate; FIRMS Newsletter, 2004, 2(2): 8-9; Forensic Explosives Laboratory, Dstl. Fort Halstead, Sevenoaks, Kent TN TN14 7BP.

* cited by examiner

*Primary Examiner* — Arlen Soderquist
(74) *Attorney, Agent, or Firm* — Krieg DeVault LLP

(57) ABSTRACT

Methods and systems are provided that utilize measured isotopic abundance data to correlate a product to the synthesis process by which it was made. By utilizing the principles described herein, isotopic process profiles for synthetic products can be constructed, products of unknown origin can be inferentially identified to the processes by which they were made, and synthesis processes can be monitored for consistency of process parameters.

33 Claims, 6 Drawing Sheets

TRACING PROCESSES BETWEEN PRECURSORS AND PRODUCTS BY UTILIZING ISOTOPIC RELATIONSHIPS

CROSS-REFERENCE TO RELATED APPLICATIONS

The present application claims the benefit of U.S. Provisional Patent Application No. 60/803,505 filed 30 May 2006 and U.S. Provisional Patent Application No. 60/897,623 filed on 26 Jan. 2007, each of which is hereby incorporated by reference in its entirety.

BACKGROUND

The present application relates to the field of isotope analysis and, in particular, an emerging new field of analytical chemistry that is directed to the derivation of information regarding the origins of synthetic products from processes in which the amounts or ratios of isotopes in either synthetic starting materials, intermediates or products are traced.

The stable isotopic composition of matter is a way to differentiate one material from another when the materials have the same elemental composition. In the pharmaceutical industry, there is a need to trace precursors (i.e., starting materials and/or synthetic intermediates) through the manufacturing process, through the marketplace, and into various usages. Products such as active pharmaceutical ingredients (APIs), excipients of drug products, synthetic intermediates, impurities in drug products, raw materials and drug products are among those products which a pharmaceutical manufacturer may wish to trace. The ready identification of products and chemical processes would allow a pharmaceutical manufacturer to monitor its products for quality purposes as well as to act as an impediment against fraudulent "knock-offs" or counterfeits. Product tracing and identification is also desirable with regard to other types of products, such as, for example, combustible fuel, environmental analytes, foods, explosive and ammunition and paint.

There is also a need for new techniques directed to "pharmaceutical authenticity" or "pharmaceutical security," such as, for example, new techniques for investigating a suspect sample of undefined origin in furtherance of drug counterfeiting investigations and/or process patent infringement investigations. Manufacturers and regulatory authorities are confronting pharmaceutical security using multiple diverse tools, which can be categorized as overt techniques, covert techniques or forensic (analytical) techniques, the latter of which has only recently begun to receive significant attention. Purposeful misidentification of pharmaceutical materials threatens the efficacy of intermediates and end-products, consumer confidence, and the economic well-being of pharmaceutical manufacturers. Thus, pharmaceutical manufacturers and regulatory agencies have a strong interest in ensuring product authenticity and security. The main areas of concern associated with purposeful misidentification are counterfeiting, diversion (also known as countertrading), vicarious liability, theft, and patent infringement.

It is apparent from the above that there is a continuing need for advancements in the relevant field, including new methods and systems for identifying and distinguishing products and processes by which they are made. The present application provides such an advancement and provides a variety of additional benefits.

Figure 1:
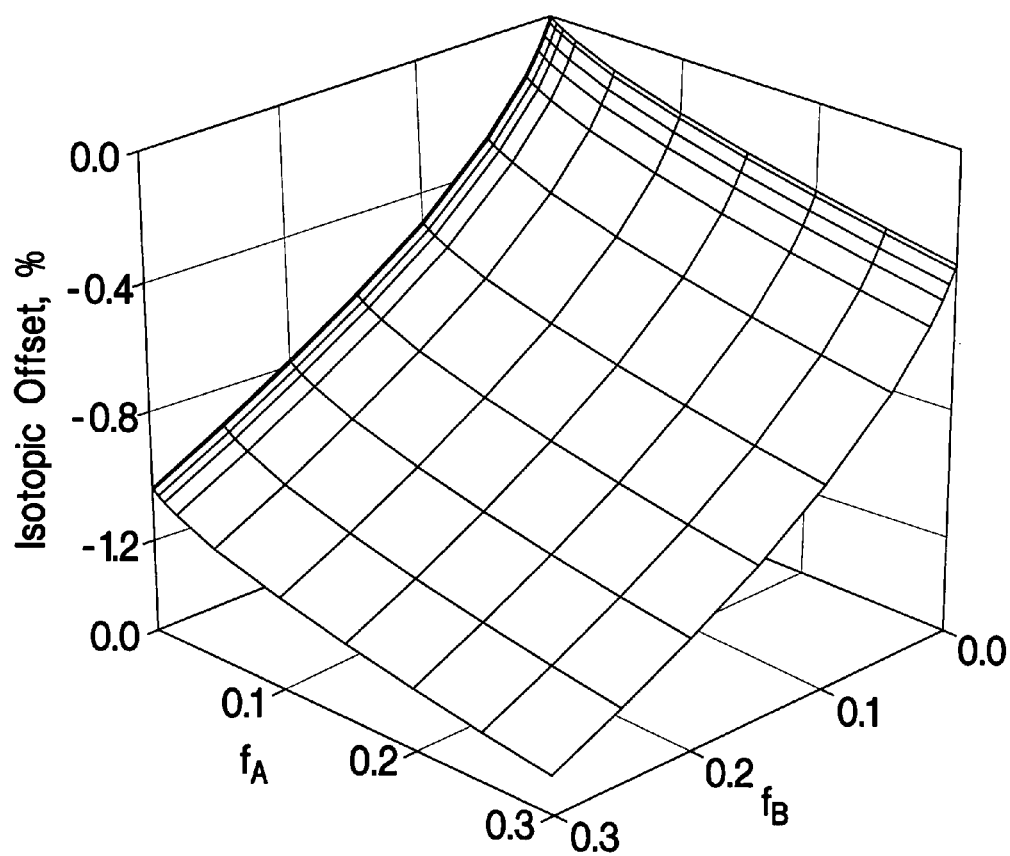
FIG. 1 is a graphic representation of the data from Table 1. The warped surface indicates the depletion of $^{13}C$ in the product relative to the isotopic composition that would be observed in the absence of isotope effects. The offset is zero if both A and B are quantitatively consumed ($f_A = f_B = 0$, the apex of the graph). Because the isotope effects on B are larger than those on A, nonzero values of $f_B$ produce greater offsets than nonzero values of $f_A$. If both $f_A$ and $f_B$ have nonzero values, the offsets are precisely additive, as indicated by eq. 7.

(b) The carbon-isotopic differences between isotopic compositions predicted and those which would be observed in the absence of isotope effects, $\delta_P^* - \delta_P$, ‰, corresponding to the values in Table 2.

SUMMARY

The present application involves an emerging new field of analytical chemistry that is directed to the derivation of information regarding the synthetic origins of a product from the differences in the amounts or ratios of isotopes in upstream precursors and final products. In this application, methods and systems are provided for constructing isotopic process profiles for a synthetic product, isotopically-inferentially identifying products of unknown origin to the processes by which they were made, and monitoring synthesis processes for consistency of process parameters. As used herein, the term "isotopic process profile" refers to a collection of isotopic data representing distinctive isotopic features or characteristics of a synthesis process used to make a composition, and is intended to have the same meaning as the term "isotopic pedigree" set forth in the priority applications. The term "isotopic composition profile" is used to refer to a collection of isotopic data representing distinctive isotopic features or characteristics of a composition, and is intended to have the same meaning as the term "isotopic fingerprint" set forth in the priority applications.

The application provides in one aspect a method for constructing an isotopic process profile for a first product made using a known synthetic process that includes (1) obtaining a first isotopic composition profile for the first product and a second isotopic composition profile for one or more starting material used to make the first product; (2) determining isotopic fractionation values for one or more reaction steps in the known synthetic process; and (3) providing a database that includes a plurality of data selected from the group consisting of (i) the first isotopic composition profile for the first product, (ii) the second isotopic composition profile for one or more starting material used to make the first product, and (iii) isotopic fractionation values for one or more reaction steps in the known synthetic process; wherein the database is an isotopic process profile of the product. In one manner of practicing the method, each isotopic composition profile comprises a plurality of data points, each data point defined as the concentration of an isotope or the ratio of two stable isotopes of an element analytically determined to be intrinsically present in the product. In another approach, at least one of the isotopic composition profiles comprises concentration or ratio data for a plurality of stable isotopes intrinsically present in the product. The product can be, for example, a compound, an active pharmaceutical ingredient, an excipient and a bulk drug product. In one embodiment, the isotopic process profile is recorded on a tangible medium such as, for example, a machine readable medium.

In another aspect of the application, there is provided a method for using the isotopic process profile that includes (1) identifying a second product of undefined origin; (2) obtaining an isotopic composition profile for the second product; (3) determining within an acceptable error whether the second product was made using the known synthetic process by comparing the isotopic composition profile for the second product to the isotopic process profile. In one form of the application, the method further includes comparing the isotopic composition profile for the second product to isotopic composition profiles for one or more similar products made using other synthetic processes, other starting materials or other synthetic process and other starting materials. In another form of the application, the method further includes making assumptions regarding the potential isotopic abundance values for starting materials used to make the second product.

In yet another aspect, the application provides a method for determining whether a product of undefined origin was made by a first known synthetic process. The method includes (1) obtaining a first isotopic composition profile for the product; (2) providing fractionation information regarding the first known synthetic process, the starting materials used to make the product, or both; and (3) inferentially determining whether the product of undefined origin was made by the first known synthetic process by comparing the first isotopic composition profile to fractionation information. The isotopic composition profile can include, for example, a plurality of data points, each data point defined as the concentration of an isotope or the ratio of two isotopes of an element analytically determined to be intrinsically present in the product. The fractionation information can include, for example, information of one of the following types: (i) a second isotopic composition profile for one or more of the starting materials used to make the product, (ii) a third isotopic composition profile for a first comparative sample of product made using the known synthetic process and different starting materials, (iii) a third isotopic composition profile and a fourth isotopic composition profile for starting materials used to make the compound in the comparative sample, or (iv) a fifth isotopic composition profile for the starting materials used to make a second comparative sample product and a calculated isotopic composition profile determined to be present in the second comparative sample made using the starting materials and the known synthetic process.

In one representative example of the method, the known synthetic process is known only by its fractionation values corresponding to the isotopes evaluated. In another representative example, the known synthetic process is known by the degree of reaction completeness for each starting material and synthetic intermediate of the synthetic process. In yet another example, the known synthetic process is known by the isotopic fractionations associated with each reaction in the synthetic process. In still another example, the known synthetic process is known by the degree of reaction completeness for each starting material and each synthetic intermediate and the isotopic fractionations associated with each reaction in the synthetic process. The first isotopic composition profile can also advantageously have associated therewith a sampling error value based upon its pooled standard error. In alternative examples of the method, the first isotopic composition profile includes at least three data points, at least four data points, at least five data points, at least six data points, at least seven data points or at least eight data points. In one embodiment, the first isotopic composition profile is provided in machine readable form. In certain preferred embodiments, the element is a light element. Also in certain preferred embodiments, the product is selected from the group consisting of a chemical product, a petroleum sample, a pharmaceutical product, a biomedical sample, a paint sample, an explosive-ammunition sample and a combustible fuel sample. The product can be, for example, an API, a drug product, an excipient of a drug product and an impurity of a drug product.

The application provides in still another aspect a method for monitoring process quality of a chemical synthesis process. The method includes (1) defining an acceptable range of isotopic abundance at an intermediate point or an end point in the chemical synthesis process for at least one stable isotope, the acceptable range encompassing isotopic abundance values that exist when the process is proceeding in an acceptable manner; (2) periodically extracting samples from the chemical synthesis process at the intermediate point or the end point; (3) measuring the actual isotopic abundance for the at least one stable isotope in the samples; and (4) comparing the actual isotopic abundance to the acceptable range to determine whether the chemical synthesis process is proceeding in an acceptable manner. The acceptable range of isotopic abundance can be defined, for example, by defining an acceptable range of isotopic abundance at an intermediate point or an end point in the chemical synthesis process for at least two stable isotopes, the acceptable range encompassing isotopic abundance values that exist when the process is proceeding in an acceptable manner The application also provides a system for monitoring process quality of a chemical synthesis process that includes (1) a sample extraction device operable to periodically obtain samples from a process stream for the chemical synthesis process at an intermediate point or an end point in the process; (2) a measuring instrument operable to receive the samples from the extraction device and determine actual isotopic abundance information for one or more isotopes in the samples; and (3) a computer processor operable to store and display the isotopic abundance information. In one embodiment, the system also includes a feedback loop operably connected to the computer processor to adjust process parameters in the chemical synthesis process using defined routines if the actual isotopic abundance information is outside acceptable ranges.

In another aspect of the application there is provided a method for making a new product batch that has a unique isotopic composition profile different than a previously-made product batch with the same molecular content. The method includes adjusting at least one aspect of the manufacturing process for the product in a manner selected from the group consisting of (i) selecting a starting material having a different isotopic composition profile, (ii) identifying a chemical reaction in the process that has an isotope effect, and halting the reaction at a different stage short of completion, (iii) identifying a chemical reaction in the process that has an isotope effect, and making the limiting reagent one that is not used to derive the isotopic composition profile of the product, (iv) altering the amount of the limiting reagent that is available for reaction, and (v) mixing into the product an excipient having a different isotopic composition profile.

Further embodiments, forms, features and aspects of the present application shall become apparent from the detailed description and figures provided herewith.

DETAILED DESCRIPTION OF SELECTED EMBODIMENTS

For the purpose of promoting an understanding of the principles described herein, reference will now be made to the embodiments set forth herein and specific language will be used to describe the same. It will nevertheless be understood that no limitation of the scope of the application is thereby intended. Any alterations or further modifications of the described embodiments and any further applications of the principles of the inventions described herein are contemplated as would normally occur to one skilled in the art to which the application relates.

The present application provides methods and systems for using analytical tools, particularly stable isotope analysis techniques, to correlate information regarding the stable isotope content of starting materials, intermediates and reaction products to the specific synthesis process used to make or modify the products. The application also provides ways to use such information for precise control or understanding of synthesis processes, and for correlating sample products with synthesis processes using isotopic information from the sample together with independently obtained information. For ease of description, the present specification provides descriptions predominantly with reference to synthesis processes used to make pharmaceutical products. It is to be understood, however, that the application is equally applicable to a wide variety of other products including, but not limited to combustible fuel, environmental analytes, foods, explosive and ammunition and paint.

The present application involves the observation that products, such as, for example, pharmaceutical products, can be characterized, or "fingerprinted," by measuring and comparing the highly-specific stable isotope concentrations or isotopic ratios of one or more isotopes therein. As used herein, the term "product" is used to identify a wide variety of materials such as, for example, compounds, starting materials, active pharmaceutical ingredients, synthetic intermediates, excipients or bulk phase drugs.

In one manner of utilizing the principles described herein, the isotopes measured in the analysis are naturally existing, low-molecular-weight, stable isotopes, such as, for example, light isotopes of carbon, nitrogen, hydrogen and oxygen as they occur in their "natural" or ambient concentrations. These isotopes are intrinsic to nearly all chemical compounds, including pharmaceutical components, active pharmaceutical ingredients (APIs), excipients, and bulk phase medicines in final dosage form. Thus, the practice of the methods described herein does not require the addition of any materials (i.e., taggants) into the process, but can be used for the detection of isotopes that are inherently in the compounds from their origins. It is to be understood, however, that the principles described herein can also be applied to products and processes that include taggants. The techniques utilized in various embodiments of the application are Internationally standardized by the International Atomic Energy Agency (IAEA), use statistically defined numerical data, and are compatible with other types of security and/or identification techniques such as, for example, Radiofrequency Identification (RFID) technology.

As used herein, the term "stable isotopes" refers to simple mass variants of chemical elements whose masses are determined by the number of protons and neutrons in a given element's nucleus. For example, carbon-12 ($^{12}C$) is composed of six neutrons and six protons. For reference, $^{12}C$ accounts for about 98.89 percent of all natural carbon. By contrast $^{13}C$ is composed of seven neutrons and six protons, and accounts for about 1.11 percent of carbon. Thus, the application involves methods for distinguishing compounds and products and processes that are fully operational utilizing naturally occurring isotopic variations in isotopic abundance Other common stable isotope pairs include nitrogen ($^{14}N$ and $^{15}N$), oxygen ($^{16}O$ and $^{18}O$), hydrogen ($^{2}H$ and $^{1}H$), and so on. Some elements also have radioactive isotopes, but in practice these are only measurable in a few elements. Radioactive $^{14}C$, for example, represents only about 1 part per trillion of all natural carbon. By contrast, stable isotopes are non-radioactive and exist naturally in pharmaceuticals and in nearly all other common materials. Therefore, nothing needs to be added to pharmaceutical products to isotopically trace them.

Scientists have used stable-isotope ratios to trace the source, or "isotopic provenance," of natural materials since the 1950s, when isotope-ratio mass spectrometers first became available. Among the 112 elements, 62 are known to have more than one stable isotope, and 40 have more than two stable isotopes. The elements that have more than two isotopes have 222 isotopes. The elements that have two or more isotopes have 266 isotopes. In view of the large number of stable isotopes that are currently known, there are many different isotopic ratios that can serve as tracers and can be utilized as described herein. By choosing just three or four ratios of various stable isotopes in a certain product, an estimated upper limit of specificity that reaches one-to-millions, even one-to-billions, can be achieved.

Even if only the common light elements of carbon, hydrogen, oxygen, nitrogen and sulfur were used, there are 13 different stable isotopes that can be employed in the methods described herein. These 13 stable isotopes provide ample means for providing a highly specific stable isotopic identification for nearly any product or chemical process desirably traced or desirably identified as will be explained further herein.

To briefly address matters of terminology and semantics, isotopic results are typically expressed in either atom percent of the less abundant isotope or delta values (parts per thousand differences from a standard). For example, with respect to carbon, isotopic results are presented as:

$$\delta^{13}C\ (‰) = [(R_{sample}/R_{standard}) - 1] * (1000)$$

where: $R_{smpl}$=the $^{13}C/^{12}C$ ratio of the sample material and the $R_{std}$ is the $^{13}C/^{12}C$ ratio of an International Atomic Energy Authority standard (known as "VPDB") whose $^{13}C/^{12}C$ ratio has been defined as the official zero point of the carbon-isotopic scale. Other stable isotope ratios are similarly expressed.

Mass spectroscopy is the tool of choice for determining isotope concentrations or ratios. A precision of 10 ppm (i.e., the difference between $^{13}C/^{12}C$=0.0112000 and 0.0112001) can be attained for measurements of carbon and oxygen isotope ratios in the mass spectrum of $CO_2$. The precision attainable for isotopic analysis of any molecule containing H, and therefore susceptible to hydrogen-transfer reactions during ionization and analysis, is abysmally low. Accordingly, all high-precision isotopic analyses are based on the conversion of the analyte to an H-free, common-denominator molecule that can be readily compared to an isotopic standard. Carbon dioxide and carbon monoxide serve for C and O, $N_2$ for nitrogen, $H_2$ for hydrogen (with corrections for unavoidable H transfers, the isotope effects being so large that the corrections are tolerable), and $SO_2$ or $SF_6$ for sulfur.

The required conversions are straightforward. Carbon, nitrogen, and sulfur are readily converted to $CO_2$, $N_2$, and $SO_2$ by combustion and processing of the products to assure elimination of nitrogen oxides and $SO_3$. Hydrogen and oxygen are readily converted to $H_2$ and CO by pyrolysis of organic material at 1450° C. These processes convert all of the C, N, etc. in a molecule into an analyzable gas like $CO_2$ or $N_2$. As a result, isotopic analyses are compound-specific (i.e., they measure molecular-average isotopic compositions) even though isotopic fractionations are position-specific.

That difference between molecular-average analyses and position-specific effects would amount to a conflict if the objective were to measure isotope effects as precisely as possible. In the present context, the molecular averaging serves mainly to attenuate fractionations due to isotope effects. Although it is important to recognize that isotope effects are position-specific, for the purpose of practicing the methods of the present application, it is sufficient to evaluate their effects on molecular-average isotopic compositions. The dominant factor controlling isotopic compositions of large synthetic products is the isotopic composition of the synthetic precursors.

The previously stated high levels of precision are obtained in replicate analyses of gases that are handled with the utmost care to avoid any sources of isotopic fractionation. The precision obtained in replicate analyses of complex organic molecules is limited not by the mass spectrometric measurement but by variations in sample handling and by trace gases that are lost or added during conversion of samples to the common-denominator molecules cited above. For carbon, the precision is routinely better than three parts in ten thousand (<0.3‰); for nitrogen and oxygen better than five parts in ten thousand (<0.5‰); and for hydrogen better than three parts in a thousand (<3‰).

In one embodiment, analyses described herein employ ratios of isotopic concentrations. In another embodiment, simple concentration measurements of individual isotopes are used. Isotopic ratios are believed to be more consistently reproducible, and isotopic ratios may not be modified by non-nuclear physical or chemical processes or explosions such that ratios will remain intact through subsequent chemical reactions. Of course stable isotopic concentrations measurements can also be obtained by combustion and mass spectrometric analysis of either bulk phases or specific compounds by the same techniques in other specific embodiments. These concentrations instead of being expressed in ratios, i.e., $^{13}C/^{12}C$, D/H, $^{15}N/^{14}N$, $^{18}O/^{16}O$, $^{34}S/^{32}S$ etc., could merely be expressed in concentrations, e.g., 12 parts per million or 0.001 percent or parts per thousand or 0.001 weight percent, 0.001 mole percent, etc. or expressed with the measurement error, e.g., two parts per thousand plus or minus two parts per million or 0.001 mole percent plus or minus 0.0001 percent.

While the application is not intended to be limited to any particular analytical method for determining isotope amounts or ratios in a product, one technique for doing so is isotope-ratio mass spectrometry (IRMS). IRMS is relatively inexpensive, and extremely precise. In one preferred manner of detecting the isotopic ratios of nitrogen and carbon isotopes in a product, an elemental analyzer/isotope ratio mass spectrometer (EA/IRMS) is used. In an EA/IRMS, samples are introduced into a high-temperature oven where they are combusted to small molecules such as $CO_2$ or $N_2$, whose isotope ratios are subsequently measured on an isotope-ratio mass spectrometer. An EA/IRMS is therefore a useful tool for measuring nitrogen and carbon isotopes. In a preferred manner of detecting the isotopic ratios of hydrogen and oxygen isotopes in a product, a Finnigan thermal conversion elemental analyzer/isotope ratio mass spectrometer (TCEA/IRMS) is used. A TCEA/IRMS is a useful tool for measuring hydrogen and oxygen isotopes.

Stable isotopes can be routinely measured by combustion and mass spectrometric analysis of either bulk phases or of specific compounds. Bulk phases can be analyzed, for example, by either off-line combustion followed by dual-inlet isotope ratio mass spectrometry (irMS) or by on-line combustion coupled with high resolution isotope ratio monitoring/mass spectrometry (irmMS).

Given the small number of stable isotopes typically analyzed, one may wonder whether the number of combinations is too limited. There is no need for concern. For the sake of analogy, consider a combination lock with four tumblers and ten digits on each tumbler. It has $10^4$ (10,000) possible combinations. Similarly, for scale, an isotopic "combination lock" has four isotopes (C, H, N, O) and each of these isotopic "tumblers" has a dynamic range of 100 "digits." That means there is a statistical upper limit of $100^4$ (100 million) possible isotopic combinations. Chemists working in the field of pharmaceutical isotopes agree that it would cost more to counterfeit a given isotopic combination accurately than it would cost to purchase the product legally. Thus, there is essentially no incentive for identity fraud by replicating isotopic combinations.

Data regarding stable isotopic measurements can be presented as a simple list of a plurality of concentrations, a simple list of a plurality of isotopic ratios, a simple list of a plurality of mathematical products of isotopic concentrations, a simple list of a plurality of mathematical products of isotopic ratios, groups of any such lists, groups of any such mathematical products, groups of any such ratios, groups of any such concentrations, mathematical products of any such concentrations plus or minus their error added, mathematical products of any such ratios plus or minus their errors added, any of such concentrations, ratios, lists, groups and mathematical products in quadrature, isotopic ratios of any of such mathematical products, ratios of said concentrations plus or minus their errors added, any of said concentrations plus or minus their errors added, factor analysis of any such concentrations, ratios, lists, groups, and mathematical products and determinants and combinations thereof.

When reporting an isotope concentration or an isotopic ratio, it is appropriate to also communicate the degree of error associated with the measurement. The term "error" is used herein generically to refer to the deviation between a measured value and the true value of the measurement no matter how expressed. The term "precision" is used herein with regard to any group of multiple measurements to refer to the 1-sigma standard deviation of those measurements divided by the square root of the number of observations in the group of measurements. The "dynamic range" is defined herein as the range of values expected for a given type of measurement divided by the 1-sigma standard deviation of that measurement.

Fundamental statistical concepts of pooled standard deviation, dynamic range, and specificity are preferably used to describe the stable-isotopic data obtained from an isotopic measurement. Pooled standard deviations (PSD) of raw data can be calculated to derive a representative standard deviation from the whole raw data set: small numbers of replicates (viz., n=1-4) are pooled to derive an averaged standard deviation that is representative of the whole sample suite. From those pooled standard deviations, pooled standard errors (PSE) are derived which scale the uncertainty of any given sample to the number of times it was analyzed; more specifically, PSE=PSD/(square root of n−1), where n is the number of measurements performed on a given sample. The dynamic range ($R_D$) is a dimensionless parameter defined as the observed range of the results divided by the pooled 1σ-standard deviations of the measurements (i.e., $R_D=\Delta\delta/PSD$; e.g., with $\Delta\delta=10‰$ and with PSD=0.1‰, $R_D=10‰/0.1‰=100$), a quantitative parameter used to assess the granularity (or fineness) to which a measurement can be performed on a given suite of samples. With the first-order assumption that stable-isotopic values may be randomly distributed across their observed range, the probability of randomly selecting a given value would be 1/100 or 1% in the preceding example. Analogously, the probability of randomly selecting a sample with two or more specific isotopic values (each with its own ±1σ-δ) would be the product of the inverse of their composite dynamic ranges [e.g., $(PSD/\Delta\delta)_a \times (PSD/\Delta\delta)_b \times (PSD/\Delta\delta)_c = (1/100)\times(1/100)\times(1/100)=1/10^6$]. This straightforward propagation of probabilities is termed "specificity." While in some natural products, certain isotopic values may be partially correlated, this easily reproducible, first-order estimate of statistical likelihood of occurrence is advantageous for stable-isotopic characterization of a pharmaceutical composition as described herein.

It is also pertinent to consider the precision (or uncertainty) of the isotopic measurements. The precision of isotope ratios measured in an analysis in which there are only a few replicates can be calculated as the pooled standard deviation (PSD) and the pooled standard errors (PSE). Next, it is possible to estimate "1σ error bars," and to calculate dynamic ranges (DR). The DR (observed isotopic range/1σ PSD) is a dimensionless quantitative measure of the number of significantly different measurements that are possible for a given suite of samples with a specified instrument. For example, if a sample suite had a range of 10 per mil (10‰) and the instrument could measure 0.1‰, then the DR would be 100 (10‰/0.1‰).

For example, for one bulk isotopic measurement performed on a subsample of a number of homogenized drug products from a given batch, the random probability of another manufacturer producing the same bulk isotopic value is estimated at about one in one hundred, or 0.01. In fact, the probability may be less than that depending upon the isotopic ranges of the production phases. A simple calculation is based upon a conservative one-sigma value for the standard deviation in the bulk isotopic measurement of 0.1‰, with a 10‰ range in the isotopic range in the bulk materials (viz., the Dynamic Range=10‰/0.1‰=100, the probability=0.01).

The degree of error in the measurement can be reduced, or the precision increased, by measuring more than one isotopic concentration or ratio. There are a total of 13 isotopes if one limits the stable isotopic identification to the common light elements. Further reduction of the error can be accomplished by using any number of the available stable isotopes, limited only by the requirement that the element selected must be in the product.

Further, inasmuch as the specificity is inversely proportional to the product of the concentrations (statistically, the product of the dynamic ranges of each analysis), by use of a mathematical or numerical array including one or more of the above-identified mathematical products, the error of identification can even be further reduced or, "the specificity of identification can even be further increased". Still further, smaller errors of identification can be obtained by using concentrations and their error in quadrature, or in factor analysis, or in combinations thereof.

When isotopic analysis of four isotopes is performed ($\delta^{13}C$, $\delta^{15}N$, $\delta^{18}O$, $\delta^{1}H$), six bivariate isotope plots can be generated containing data from multiple samples. Clustering of the data suggests distinct synthetic pathways. Condensing three dimensions into a trivariate or ternary isotope plot gives an even higher information content for the whole data set and has a very fine 1σ grid spacing. In compensation, the sizes of error bars in a trivariate plot are vanishingly small—on average, only about 1% in each of the three dimensions—much smaller than the graph symbols themselves.

Another fundamental principle utilized by the application is that, while the isotopes of an element participate in the same chemical reactions, rates of reaction and transport of an isotope through the reaction depend on nuclidic mass, with isotopic substitutions subtly affecting the partitioning of energy within molecules. These deviations from perfect chemical equivalence are termed isotope effects. While an isotope effect is not directly observable, its existence can be inferred from its effect on isotopic abundances during the course of a chemical reaction, or between the ideal isotope-mass balance between precursors and products and the observed difference. The presence of an isotope effect in a reacting system can be expected to lead to an isotopic "fractionation," which is an observable effect generally described in terms of enrichment or depletion of the heavy isotope.

Stable-isotopic values for products versus reactants are affected by the fractionation that occurs during the reaction or reactions, and thus during a chemical or pharmaceutical manufacturing process, which results in an isotopic composition profile for the product that is different than what would otherwise be expected based upon the isotopic ideal mass-balance of the reactants. As discussed further below, isotopic fractionation between light and heavy isotopes occurs when chemical reactions do not proceed to completion (i.e., when all of the starting materials are not consumed), or when multiple products are formed, and those isotopes are unevenly distributed among the reactants and products. The two factors that determine the isotopic composition of products therefore, are the reactants and the isotopic fractionations of the synthetic reactions.

Equations relating to isotopic abundances tend to employ complex notation and can include a profusion of terms. Some of that is due to an inescapable dichotomy. Mass balances are exact when cast in terms of fractional abundances [e.g., $^{13}C/(^{12}C+^{13}C)$]. Assessments of differential rates are based on isotope ratios (e.g., $^{13}C/^{12}C$). When these systems must be blended, we employ either approximations or equations with lots of terms. For purposes of the present discussion, only four parameters require special attention. These are:

n represents the stoichiometry of the reaction, more specifically the number of atoms of a given element (e.g., carbon) in a given molecule involved in the reaction.

δ A measure of isotopic abundance, or isotopic composition, usually reported as the difference in parts per thousand, or permil (‰), from an international standard. Values of δ are linearly proportional to the isotope ratio (e.g., $^{15}N/^{14}N$). More specifically, they are based on the factor by which the isotope ratio in a sample differs from that in the international standard (seawater for H and O, a limestone for C, air for N). If the sample is depleted in the heavy isotope relative to the standard, δ will be negative. If it has the same isotopic abundance, δ=0. If it is enriched, δ>0.

ε A measure of the magnitude of an isotope effect, with consideration of primary and secondary isotopic fractionations. Like δ, it relates to the isotopic difference between two materials (e.g., reactant and product) and is usually expressed in permil. For kinetic isotope effects, in the system employed here, ε-=10‰ means that the reactant bearing the heavy isotope at the reaction site reacts 10 parts per thousand, or 1%, more slowly than the reactant bearing the light isotope. For equilibrium isotope effects, $\epsilon_{A/B}$=15‰ would mean that, at equilibrium, A was enriched in the heavy isotope by 15 parts per thousand relative to B. A and B refer to specific atomic positions that can be related by a chemical equilibrium.

f A measure of the progress of a reaction or, stated alternatively, the degree of reaction completeness. Values range from 1 to 0. In equilibria (A⇌B), f indicates the position of the equilibrium, with $f_B$=1 indicating complete conversion to B and, at any position, $f_A+f_B$=1. In irreversible reactions, $f_X$ indicates the extent to which reactant X has been consumed, with $f_X$→0 as the reaction proceeds to completion.

Stable-isotopic composition of products is a function of the isotopic composition of raw materials or precursors and processes of synthetic isotope fractionation, which is equivalent to saying that it is a function of thermodynamic and kinetic properties. To account for the mass and isotopic composition of pharmaceutical materials, these laws are fundamental:

Mass balance: $M_a+M_b=M_T$

Isotope mass balance: $M_a\delta_a+M_b\delta_b=M_T\delta_T$

Where, $M_a$, $M_b$ and $M_T$ are the masses of component a, b and their total T. $\delta_a$, $\delta_b$ and $\delta_T$ are the stable isotopic compositions of sample a, sample b and their total T. So, in a simple system (e.g., Reactants A+B→+Product T), where all components can be accounted for as "reactants" or "products," then the isotopic composition is rigorously defined by the preceding laws.

Commonly, the isotopic fraction difference, or fractionation, between reactants ($\delta_R$; viz., $\delta_A$, $\delta_B$) and a product ($\delta_P$; viz., $\delta_C$) is denoted $\Delta\delta$ (=b$\delta_P-\delta_R$), where $\delta_P$=isotopic compositions (in ‰) of the product ($\delta_P$) and reactant ($\delta_R$). More precisely and formally, the isotopic difference is denoted $\epsilon_P=[(\delta_R+1000)/(\delta+1000)-1]10^3$. Typically, the most important variable in synthetic-isotopic fractionation is the rate of the potentially-fractionating reaction. The forcing function for reaction rate may be factors such as temperature, pressure, or availability of reactants. For an isotopic effect to result in fractionation, it is necessary that the system in which the isotope effect is occurring must be arranged so that an isotopic separation can occur. If a reactant is transformed completely to yield the product, an isotopic separation which might have been visible at some intermediate point will not be observable because the isotopic composition of the product will eventually duplicate that of the reactant when all of the reactant is converted to product (the mass-balance principle). In other words, even the largest isotope effect possible will not cause any fractionation if the reaction with which it is associated occurs quantitatively. An isotopic fractionation will, however, always be observed when a reaction has an isotopic effect and the formation of product is not quantitative.

A straightforward application of synthetic-isotope fractionation in manufacturing consistency is monitoring a simple two-reagent (A+B) reaction that produces one product P. In this reaction, where reagent A is in excess, reagent B is limiting, the overall fractionation of the reaction is given by ΔA, where ΔA for a given reaction is a function of the isotopic compositions (δ) of components A, B and P.

For a pharmaceutical product, the source of each atom can be known in detail. A methyl carbon will derive from a particular synthetic reactant, an amino nitrogen from another. The measured carbon or nitrogen isotopic composition of the final product will be the weighted average of all carbon or nitrogen positions within the molecule. In turn, it will be equal to the weighted average of the isotopic compositions at the precursor positions in the synthetic reactants as modified by only two factors: (i) if the synthetic reactions are non-quantitative, any isotope effects which modulate the transfer of material from reactants to products and, (ii) in some cases, exchanges of isotopes between products and reaction media.

During batch production of pharmaceutical components, the starting materials become homogenized. As a result, each batch has a highly specific "isotopic composition profile." Furthermore, only two factors affect the isotopic ratios in pharmaceutical components: the isotopic composition of the starting materials (referred to herein as "thermodynamic fractionation" or "equilibrium isotope effects") and the isotopic fractionation that often occurs during synthesis (referred to as "kinetic fractionation" or "kinetic isotope effects"). In the language of a chemist, isotopic ratios are caused by thermodynamic and kinetic processes. There are no other known means for change. A change in either of these variables produces a drug product having a different isotopic composition profile, or fingerprint.

When chemical reactions do not proceed to completion, or when multiple products are formed, light- and heavy isotopes are commonly distributed unevenly among reactants and products. Such isotopic inhomogeneities are referred to as fractionations. In principle, the isotopic compositions of chemical products can be predicted from the isotopic compositions of the starting materials together with knowledge of the fractionations. It is important to keep in mind that the latter can be predicted quantitatively only when complete mass balances are available and when the kinetic and equilibrium isotope effects associated with all relevant chemical reactions are known accurately. Calculations provide a means of estimating ranges of variation.

While it is not intended that the application be limited by any theory, there are several possible explanations of isotope effects, i.e., of why one isotope might preferentially transfer to a given reaction product. For example, it has been observed that an equilibrium isotope effect will cause the heavy isotope to accumulate in a particular component of a system at equilibrium. It is believed that this effect results from a tendency for the heavy isotope to move preferentially to the chemical compound to which the element is bound most strongly. In addition, heavy isotopes are generally believed to preferentially partition to the more condensed phase (i.e., solid>liquid>gas). Furthermore, vapor-pressure isotope effects provide an example of a second kind of equilibrium isotope effect. They are, for the most part, normal (species containing the lighter isotope are more volatile), though inverse vapor-pressure isotope effects in which species containing the heavy isotope are more volatile are frequently encountered when D replaces H at molecular positions not affected by polar interactions in the condensed phase.

A kinetic isotope effect is said to occur when the rate of a chemical reaction is sensitive to atomic mass at a particular position in one of the reacting species. If the sensitivity to isotopic substitution exists at the position at which chemical bonding changes during the reaction, the kinetic isotope effect is described as primary. A secondary kinetic isotope effect is one in which the sensitivity to isotopic substitution occurs at an atomic position not directly involved in the reaction itself. A normal kinetic isotope effect is one in which the species containing the lighter isotope reacts more rapidly. It is believed that most primary kinetic isotope effects involving elements heavier than H are normal; some secondary kinetic isotope effects and some primary kinetic isotope effects involving H are inverse.

With regard to the above statement regarding the applicability of isotope effects to atomic positions, it is important to recognize that isotope effects pertain to the effect of isotopic substitution at a particular site within a molecule. They are, therefore, position-specific. With regard to kinetic isotope effects, during formation of bonds, it is believed that, if all other factors are equal, reactants with light isotopes ($^{12}C$, $^{14}N$, etc.) at the reaction site will tend to react more quickly than those with heavy isotopes in the same atomic positions. If bond formation is the rate-limiting step in the reaction, then light isotopes will be transferred from reactants to products more rapidly than heavy isotopes. A fractionation results, with the product being depleted in heavy isotopes relative to the reactant. The fractionation is believed to occur at or close to the reaction site. The ratio of rate constants expressing the effect of isotopic substitution at the reaction site, $^hk/^lk$, where h and l pertain to the heavy and light isotopic species, expresses the magnitude of such a primary isotope effect. When $^hk/^lk<1$, the effect is said to normal. In fact, inverse primary kinetic isotope effects ($^hk/^lk>1$) are practically unknown for heavy atoms (>H and its isotopes).

Rate effects dependent upon isotopic substitution at positions other than the reaction site are termed secondary kinetic isotope effects. They are believed to occur as a result of isotopic substitution having an effect on the distribution of electron density and as a result of changes in the masses of substituents having an effect on the partitioning of vibrational energy at the reaction site. Such secondary effects can be either normal or inverse. They are much smaller than the primary effects. Commonly, they are of detectable magnitude only at positions immediately adjacent to the reaction site. Atoms at positions other than those affected by primary or secondary effects are just along for the ride. For them, the isotopic composition of the reactant is carried unchanged into the product.

With regard to equilibrium isotope effects, if a reaction is reversible (e.g., transesterification, formation of an acetal or ketal), differences in the partitioning of vibrational energy in reactant and product structures can be more enhanced. In general, the free energy in the system will be minimized when the heavy isotope concentrates where it is bound more tightly. For example, in the reversible exchange of O between $H_2O$ and $CO_2$, $^{18}O$ accumulates preferentially in the $CO_2$. Specifically, at equilibrium at 25° C., the ratio of $^{18}O$ to $^{16}O$ in $CO_2$ is more than 40 parts per thousand larger than the same ratio in $H_2O$. Equilibrium isotope effects are also position-specific.

The magnitude of an equilibrium isotope effect can be calculated with an accuracy of a few parts per thousand for reversible reactions occurring in the gas phase. For all other cases, predictions of isotope effects are approximations. For kinetic isotope effects, calculations are based on estimates of the structure of the transition state (including effects of partial bonds). In studies of reaction mechanisms, observation of a kinetic isotope effect, coupled with consideration of the isotope effects expected to be characteristic of various transition states, can often constrain the reaction pathway. The magnitude of a kinetic isotope effect expresses the isotopic separation observed at the start of a reaction (i.e., the heavy/light isotope ratio at the reaction site in the first-formed product relative to that in the initial reactant). If the reaction proceeds to completion, quantitative transfer of atoms from reactant to product assures that the isotopic fractionation will be zero even if the reaction has a large isotope effect. The magnitude of an equilibrium isotope effect expresses the isotopic separation observed at equilibrium. It will be independent of the degree of conversion of reactants to products.

Primary, heavy-atom isotope effects range up to tens of parts per thousand (a few percent). Primary hydrogen isotope effects can be as large as a factor of two. Those occurring in synthetic reactions are more commonly hundreds of parts per thousand. The resulting isotopic differences, for all elements, range up to a few hundredths of an atom percent. These are more than a hundred times larger than the smallest variations measurable using prior techniques.

In accordance with the application, the isotopic ratios of a product of a chemical synthesis process can be predicted if information is available regarding the isotopic abundance in the starting materials and the fractionation values for the reactions. Here, in order to focus on the results, some Examples are provided without derivation.

To begin, it is helpful to consider what happens in the absence of isotope effects. In such cases, the isotopic composition of the product is the weighted average of those at all the precursor positions. As an example, consider this esterification:

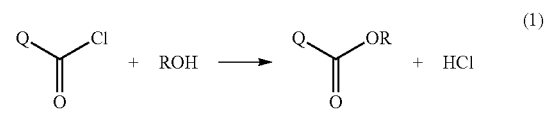

(1)

where Q and R are arbitrary organic moieties containing respectively $n_Q$ and $n_R$ carbon atoms. Standard procedures can have determined the carbon-isotopic compositions of reactants. That of the product ester can then be calculated from a mass balance:

$$^{13}C \text{ in reactants} = {}^{13}C \text{ in products} \quad (2a)$$

Using the δ notation, eq. 2a takes this form:

$$(n_Q+1)\delta_{QCOCl}+n_R\delta_{ROH}=(n_Q+n_R+1)\delta_{QCOOR} \quad (2b)$$

In this expression, $\delta_{QCOCl}$ and $\delta_{ROH}$ are the measured isotopic compositions of the acyl chloride and the alcohol and $\delta_{QCOOR}$ is the isotopic composition of the product ester. Equation 2b contains no term for HCl, the second product, because it contains no carbon. Rearrangement of eq. 2b yields an expression for $\delta_{QCOOR}$, the isotopic composition of the product ester:

$$\delta_{QCOOR} = \frac{(n_Q+1)\delta_{QCOCl}+n_R\delta_{ROH}}{n_Q+n_R+1} \quad (3)$$

Equation 2b is a specific example of a mass balance. In general, for the reaction $$A+B \rightarrow P \quad (4)$$

the corresponding isotopic mass balance is $$n_P\delta_P = n_A\delta_A + n_B\delta_B \quad (5)$$

where A, B, and P contain $n_A$, $n_B$, and $n_P$ atoms of the element under consideration. For convenience in the following discussion, we will define $$\delta_P^* \equiv \frac{1}{n_P}(n_A\delta_A + n_B\delta_B) \quad (6)$$

where $\delta_P^*$ is the isotopic composition expected for the product in the absence of isotope effects.

Next, it is helpful to consider the fractionation that results from kinetic isotope effects in an irreversible reaction that occurs in a closed system. This is pertinent to common, batch-wise syntheses. For a reaction system like that in eq. 4 we have $$\delta_P = \delta_P^* - \frac{1}{n_P}\left[\frac{f_A}{1-f_A}\ln f_A(\varepsilon_{A1}+\varepsilon_{A2}+\ldots) + \frac{f_B}{1-f_B}\ln f_B(\varepsilon_{B1}+\varepsilon_{B2}+\ldots)\right] \quad (7)$$

where $\varepsilon_{A1}$ and $\varepsilon_{B1}$ are the primary kinetic isotope effects at the reaction sites in A and B, respectively, and $\varepsilon_{A2}$, $\varepsilon_{B2}$ . . . are secondary isotope effects, if any are significant (see Note 1 below for information about the measurement of kinetic isotopic effects). This expression is based on eq. 6, above. It shows that, to whatever extent a reactant is not consumed quantitatively (f>0), the isotopic composition of the final product will fall slightly below that expected in the absence of isotope effects (i.e., the product will be depleted in the heavy isotope relative to the reactants). The key factors in the bracketed term are the coefficients based on f and the values of ε. Assuming that normal isotope effects are dominant, both are negative. To illustrate the utility of eq. 7, we will consider two examples.

Note 1. Isotope effects can be measured most precisely by measuring isotopic compositions as a function of yield. The first-formed products will be depleted in the heavy isotope (or, equivalently, enriched in the light isotope). When conversion of reactants to products is quantitative, the isotopic composition of the product will match that of the reactants. The slope of the line linking these points on a plot of δ values vs. the yield provides the value of ε. A less precise but very serviceable estimate of ε can be obtained using the "low-conversion approximation":

$$\varepsilon = \delta_P' - \delta_P^* \quad (N1)$$

where $\delta_P'$ is the isotopic composition of the first-formed product and $\delta_P^*$ is defined by eq. 6. For the case in which P derives from reactants A and B, these approaches are applicable when either A or B is unaffected by isotope effects. If, for example $\Sigma\varepsilon_A=0$, the ε in eq. N1 would be $\Sigma\varepsilon_B$. More elaborate approaches are required when both A and B are isotopically fractionated during the formation of P.

The first example illustrating the utility of eq. 7 pertains to a specific case in which A is the limiting reactant and B is present in excess. At the conclusion of the reaction, therefore, $f_A=0$ and $f_B$ has some finite value, say 0.3 (corresponding to 70% consumption of B). Since carbon atoms from A are transferred quantitatively into the product, the A-derived positions in the product will have an isotopic compositions equal to those in the reactant. Mathematically, this is expressed by the A-related terms in eq. 7. The coefficient for $(\varepsilon_{A1}+\varepsilon_{A2}+\ldots)$ will be zero when $f_A=0$. As a result, the A-related terms will not contribute to the difference between $\delta_P$ and $\delta_P^*$. On the other hand, the coefficient for $(\varepsilon_{B1}+\varepsilon_{B2}+\ldots)$ will be −0.5 when $f_B=0.3$. Accordingly, the B-derived positions in the product will be depleted in $^{13}C$ relative to those in B by an amount equal to half the summed isotope effects. The resulting difference between $\delta_P$ and $\delta_P^*$ can be much smaller, since that value is divided by the total number of carbon atoms in the product.

A second, more general example illustrating the utility of eq. 7 is summarized in Table 1. This information relates to a case in which the product, P, contains 15 carbon atoms and the sums of the primary and secondary isotope effects on reactants A and B ($\Sigma\varepsilon_A$, $\Sigma\varepsilon_B$) are −10% and −30%, respectively. The tabulated values are the offsets relative to the isotopic composition that would be observed in the absence of any isotope effects (that is, $\delta_P-\delta_P^*$). Inspection shows that the results are in accord with the guidelines summarized above. At $f_A=0$ and $f_B=0.3$, for example, the offset is −1.03%. This is $-\frac{1}{15}^{th}$ (=−$1/n_P$) of (−0.516)(−30%) where −0.516=$f_B\cdot\ln f_B/(1-f_B)$.

TABLE 1

Example[a] of isotopic offsets, $\delta_P - \delta_P^*$, ‰, calculated using eq. 7[b]

| Yield A→ | | 100% | 99.9 | 99.5 | 99 | 98 | 95 | 90 | 80 | 70 |
|---|---|---|---|---|---|---|---|---|---|---|
| B | f | 0 | 0.001 | 0.005 | 0.01 | 0.02 | 0.05 | 0.1 | 0.2 | 0.3 |
| 100% | 0 | 0.00 | 0.00 | −0.02 | −0.03 | −0.05 | −0.11 | −0.17 | −0.27 | −0.34 |
| 99.9 | 0.001 | −0.01 | −0.02 | −0.03 | −0.04 | −0.07 | −0.12 | −0.18 | −0.28 | −0.36 |
| 99.5 | 0.005 | −0.05 | −0.06 | −0.07 | −0.08 | −0.11 | −0.16 | −0.22 | −0.32 | −0.40 |
| 99 | 0.01 | −0.09 | −0.10 | −0.11 | −0.12 | −0.15 | −0.20 | −0.26 | −0.36 | −0.44 |
| 98 | 0.02 | −0.16 | −0.16 | −0.18 | −0.19 | −0.21 | −0.26 | −0.33 | −0.43 | −0.50 |

TABLE 1-continued

Example[a] of isotopic offsets, $\delta_P - \delta_P^*$, ‰, calculated using eq. 7[b]

| Yield B | A→ f | 100% 0 | 99.9 0.001 | 99.5 0.005 | 99 0.01 | 98 0.02 | 95 0.05 | 90 0.1 | 80 0.2 | 70 0.3 |
|---|---|---|---|---|---|---|---|---|---|---|
| 95 | 0.05 | −0.32 | −0.32 | −0.33 | −0.35 | −0.37 | −0.42 | −0.49 | −0.58 | −0.66 |
| 90 | 0.1 | −0.51 | −0.52 | −0.53 | −0.54 | −0.56 | −0.62 | −0.68 | −0.78 | −0.86 |
| 80 | 0.2 | −0.80 | −0.81 | −0.82 | −0.84 | −0.86 | −0.91 | −0.98 | −1.07 | −1.15 |
| 70 | 0.3 | −1.03 | −1.04 | −1.05 | −1.06 | −1.09 | −1.14 | −1.20 | −1.30 | −1.38 |

[a] Reaction A + B → P with summed kinetic isotope effects on A and B of −10 and −30‰, respectively. The product, P, is assumed to contain 15 carbon atoms.
[b] Example: for $f_A = 0.02$ (98% yield based on A) and $f_B = 0.2$ (80% yield based on B), the product is depleted in $^{13}C$ by 0.86‰ relative to the $^{13}C$ content that would be observed in the absence of isotope effects.

The same data are summarized graphically in FIG. 1. It is evident in this data that small variations in f cause increasingly large variations in the isotopic offset as f→0. If the aim is to obtain isotopic stability in the product, it will be easier to achieve if the yield is 80% than if it's 99%. To examine this quantitatively, we can evaluate the partial derivatives of $\delta_P$ with respect to $f_A$ and $f_B$.

$$\frac{\partial \delta_P}{\partial f_A} = \frac{\sum \varepsilon_A}{n_P}\left[\frac{1}{1-f_A} + \frac{\ln f_A}{(1-f_A)^2}\right] \quad (8)$$

$$\frac{\partial \delta_P}{\partial f_B} = \frac{\sum \varepsilon_B}{n_P}\left[\frac{1}{1-f_B} + \frac{\ln f_B}{(1-f_B)^2}\right]$$

Then, to quantify the dependence of variations in $\delta_P$ on variations in $f_A$ and $f_B$, we can write $$\sigma_{\delta_P}^2 = \left(\frac{\partial \delta_P}{\partial f_A}\right)^2 \sigma_{f_A}^2 + \left(\frac{\partial \delta_P}{\partial f_B}\right)^2 \sigma_{f_B}^2 \quad (9)$$

Where the $\sigma^2$ terms are variances in the indicated quantities.

The conditions required to limit variations in $\delta_P$ depend on $n_P$, $\Sigma \varepsilon_A$, $\Sigma \varepsilon_B$, $f_A$, and $f_B$. If $n_P$ is large or if the isotope effects are small, permissible variations in $f_A$ and/or $f_B$ can be relatively large. For any specific case, calculations based on eqs. 8 and 9 are required. To obtain at least a preliminary view, we will examine two cases, both based on the values of $n_P$, $\Sigma \varepsilon_A$, and $\Sigma \varepsilon_B$ used to construct Table 1 and FIG. 1.

Case 1. Reactant A in excess, reactant B consumed almost quantitatively. Assume $f_B = 0.02$ and $\sigma_{f_B} = 0.003$. Solve eqs. 8 and 9 to determine tolerable values of $\sigma_{f_A}$ as a function of $f_A$ if $\sigma_{\delta_P}$ is to be less than 0.1% (i.e., a 95% confidence interval for $\delta_P$ of ±0.2‰).

Case 2. Reactant B in excess, reactant A consumed almost quantitatively. Assume $f_A = 0.02$ and $\sigma_{f_A} = 0.003$. Solve eqs. 8 and 9 to determine tolerable values of $\sigma_{f_B}$ as a function of $f_B$ if $\sigma_{\delta_P}$ is to be less than 0.1% (i.e., a 95% confidence interval for $\delta_P$ of ±0.2‰).

Figure 2:
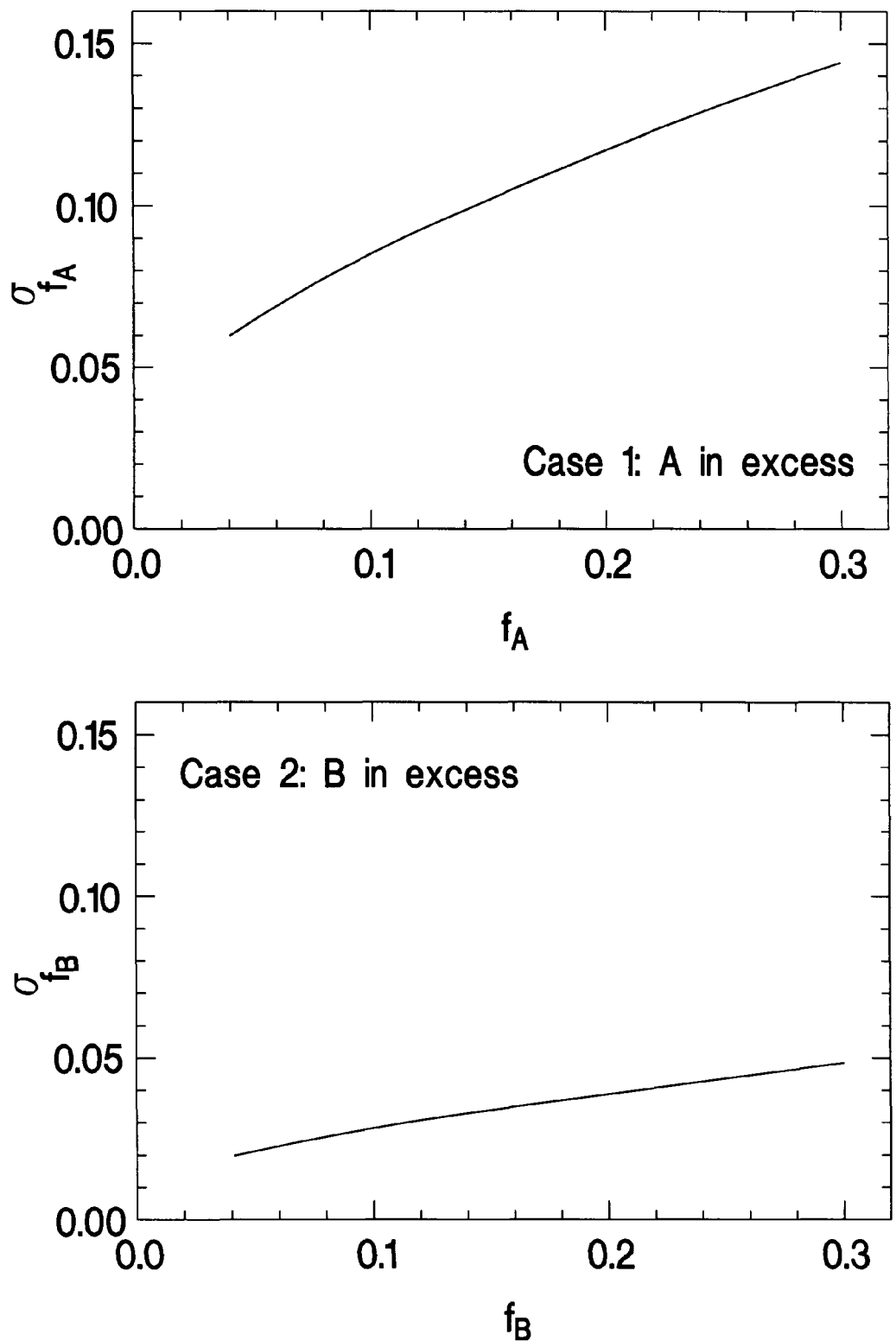
FIG. 2 includes two plots showing that variations in yield will cause $\delta_P$ to vary by ±0.2‰. Larger variations are tolerable in case 1 because the sum of the isotope effects on reactant A is −10‰ whereas that on reactant B is −30‰. In case 1, permissible variations in the yield based on A are enormous. Variations between 70 and 90% (equivalent to $\sigma_{f_A} = 0.05$) would be well below the limit (about 0.12 at $f_A = 0.2$, equivalent to 80% yield). In case 2, variations between 72 and 88% would still be tolerable.

In each case, it is assumed that "almost quantitative" means that the yield based on the limiting reactant is 98% and that variations in that yield are small. It is then pertinent to consider how greatly the consumption of the excess reactant can vary before variations in $\delta_P$ exceed ±0.2‰. The results, summarized graphically in FIG. 2, show that wide variations in yield can often be tolerated without causing significant variations in $\delta_P$.

It is also useful to consider the fractionation that results from equilibrium isotope effects in a reversible reaction that occurs in a closed system. If a synthetic reaction is readily reversible (e.g., transesterification, formation of a ketal), isotopic fractionations will result from equilibrium isotope effects. In this case, for $$A + B \rightleftharpoons P \quad (10)$$

the mass balance leading to $\delta_P^*$ is unchanged from eqs. 5 and 6, but in place of eq. 7 we have $$\delta_P = \delta_P^* - \frac{1}{n_P}\left(f_A \sum \varepsilon_{A/P} + f_B \sum \varepsilon_{B/P}\right) \quad (11)$$

where $f_A$ and $f_B$ are the fractions of reactants A and B, respectively, that remain at equilibrium, and $\varepsilon_{A/P}$ and $\varepsilon_{B/P}$ are equilibrium isotope effects. A summation is used because isotope effects are likely to occur at multiple positions. For a specific position, x, in the reactant and the related position, y, in the product, the precise relationship is $\varepsilon_{Ax/Py} = \alpha_{Ax/Py} - 1$, where

$$\alpha_{Ax/Py} = \frac{R_{Ax}}{R_{Py}} = \frac{\delta_{Ax}+1}{\delta_{Py}+1} \quad (12)$$

This notation arises because an equilibrium isotope effect directly controls the ratio of isotope ratios. As shown, $\alpha_{Ax/Py}$ is the "fractionation factor" relating the isotope ratio ($R = {}^{13}C/{}^{12}C$) at position x in A to that at position y in P. If the heavy isotope is enriched in the product, $R_{Py}$ will be greater than $R_{Ax}$, $\alpha_{Ax/Py}$ will be less than 1, and $\varepsilon_{Ax/Py}$ will be negative.

For carbon, equilibrium isotope effects in synthetic reactions are usually smaller than kinetic isotope effects. For nitrogen and oxygen, in contrast, equilibria are likely to involve replacement of an N—H or O—H bond with a bond to a heavy atom. In such cases, the equilibrium isotope effect can equal or exceed commonly encountered kinetic isotope effects. Moreover, whereas numerous atoms of C will form the skeleton of the molecule, atoms of N and O will be rarer. Accordingly, values of $n_P$ will be smaller and effects on $\delta_P$ will be larger for these elements.

Figure 3:
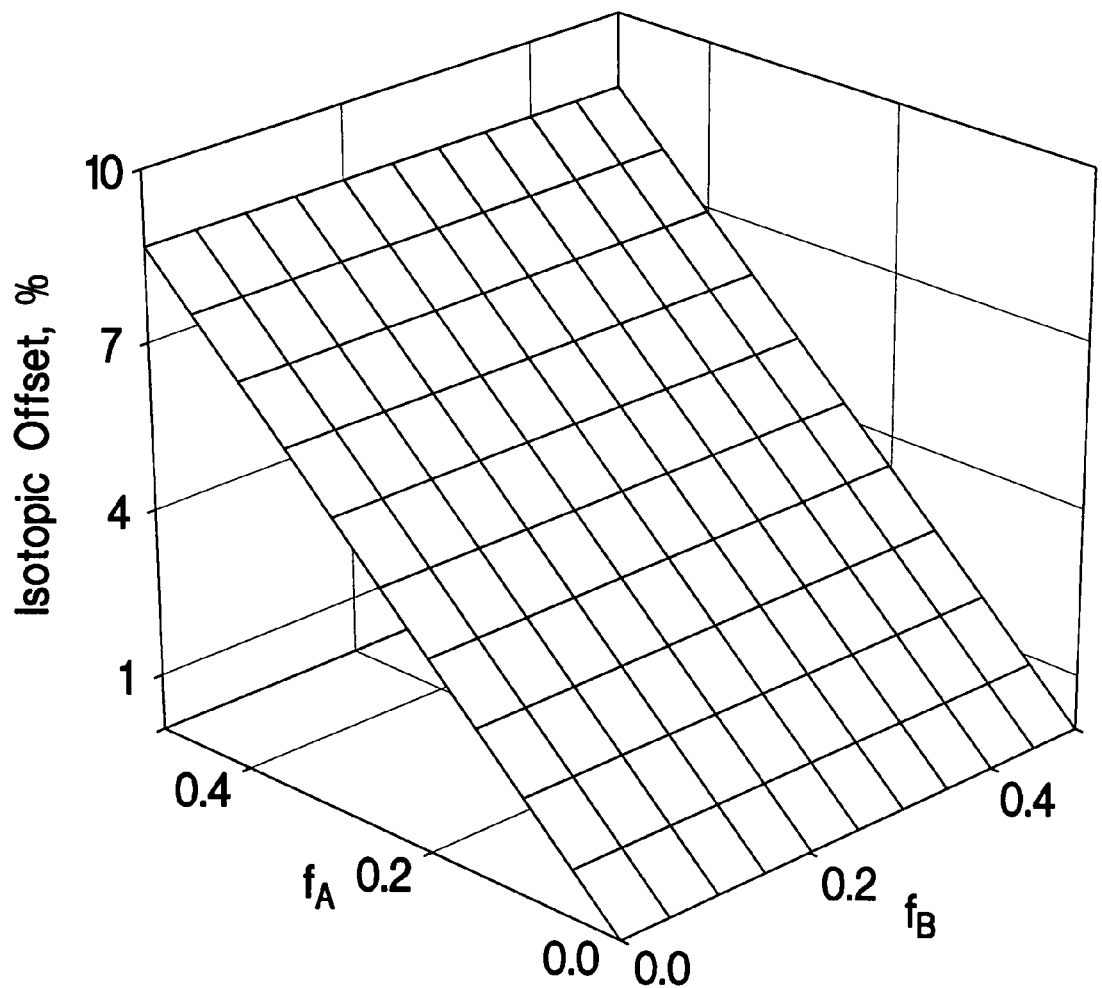
FIG. 3 is a plot showing variations in the isotopic offset, $\delta_P - \delta_P^* = -(1/n_P)(f_A \Sigma \epsilon_{A/P} + f_B \Sigma \epsilon_{B/P})$, as a function of $f_A$ and $f_B$, for a case involving only equilibrium isotope effects (eq. 11). It's been assumed that a product containing six oxygen atoms is formed from reactants containing four and two oxygen atoms. The former are present as OH groups in A but are bound in C—O—C linkages in the product, P. As a result, there is an inverse equilibrium isotope effect of 26‰ at each of four oxygen atoms in the product (P enriched in $^{18}O$ relative to A). The two oxygen atoms inherited from reactant B are not involved in the reaction.

Equilibrium isotope effects can be normal or inverse, leading products to be either depleted or enriched in heavy isotopes relative to the reactants. Apart from that difference, versions of Table 1 and FIG. 1 pertaining to fractionations arising from equilibrium isotope effects differ from their kinetically fractionated counterparts only in that isotopic offsets would vary linearly with values of f. An example is shown in FIG. 3. I FIG. 3 it is assumed that a product containing six oxygen atoms is formed from reactants containing four and two oxygen atoms. The former are present as OH groups in A but are bound in C—O—C linkages in the product, P. As a result, there is an inverse equilibrium isotope effect of 26‰ at each of four oxygen atoms in the product (P enriched in $^{18}O$ relative to A). The two oxygen atoms inherited from reactant B are not involved in the reaction. Referring to eq. 11, we have $n_P=6$, $\Sigma\epsilon_{A/P}=4\times-26=-104$, and $\Sigma\epsilon_{B/P}=0$. The planar surface shown in FIG. 3 summarizes variations in the isotopic offset, $(1/n_P)(f_A\Sigma\epsilon_{A/P}+f_B\Sigma\epsilon_{B/P})$, as a function of $f_A$ and $f_B$. As shown, $\delta_P$ is independent of $f_B$ but increases relative to $\delta_P^*$ depending on the extent to which formation of the product from A is not quantitative ($f_A=0$ corresponds to complete consumption of A).

Special attention is required for the case of hydrogen. Because hydrogen isotope effects are so much larger than those affecting heavier atoms, those equations are not applicable to H. Equation 11 would be a useful guide to values of $\delta_P$, but could be in error by more than 20‰.

The sensitivity of $\delta_P$ to variations in f will in general be lower for equilibrium than for kinetic isotope effects. This is because, in the equilibrium case, $$\frac{\partial \delta_P}{\partial f_A} = \frac{\sum \varepsilon_A}{n_P} \qquad (13)$$

$$\frac{\partial \delta_P}{\partial f_B} = \frac{\sum \varepsilon_B}{n_P}$$

and, for all values of f<0.32 (i.e., for yields greater than 68% and likely to be economically practical), $$\frac{1}{1-f} + \frac{\ln f}{(1-f)^2} > 1 \qquad (14)$$

where the left side of the inequality is the coefficient for $\Sigma\epsilon/n_P$ in eq. 8 and 1 is the coefficient in eq. 13.

Isotopic analysis can provide a wealth of information about a manufacturing process during which raw materials are manufactured into intermediates, active agents, such as, for example, pharmaceutical ingredients (APIs) and, finally, into final products, such as, for example, drug products. When considering multi-step manufacturing processes, it is important to recognize that every reaction (or sub-reaction, depending upon the terminology used) has its own isotopic fractionation ($\Delta\delta$), and $\Delta\delta$'s are additive. For example, the following series represents a multi-step reaction, in which each line represents a sub-reaction, each letter represents one or more reactants (left of arrow) or products (right of arrow) in a given sub-reaction, and each sub-reaction has associated therewith an isotopic fractionation value:

A→B $\Delta\delta_{B-A}$

B→C $\Delta\delta_{C-B}$

C→D $\Delta\delta_{D-C}$

The overall reaction, which can be identified as reaction A→D, has an isotopic fractionation value ($\Delta\delta_{D-A}$) that can be determined by adding $\Delta\delta_{B-A}+\Delta\delta_{C-B}+\Delta\delta_{D-C}$. As such, the relationships described herein can be utilized to either track individual sub-reactions or overall syntheses that involve multiple sub-reactions by determining the isotopic composition profiles of select starting materials, intermediates and/or products.

In addition to the fractionation that occurs in a synthetic chemical reaction pathway, as described in detail herein, isotopic fractionation can also result from other types of processes. For example, fractionation can occur during crystallization processes and can result from mixing operations and/or size separation processes such as sieving or particle sorting.

The present application provides methods that can be advantageously used in connection with continuous manufacturing processes, or in connection with batch manufacturing processes. As used herein, the term "batched material" refers to a quantity of a material that is substantially homogenous, i.e., characterized in that multiple samples from a batched material should have the same isotopic composition profile as determined within the error of analysis and sampling. The term "batched material" includes, for example, starting materials for a manufacturing process (whether the process is a continuous manufacturing process or a batch manufacturing process), intermediates of a chemical synthesis process that are isolated from the process and homogenized in a container, ingredients of pharmaceutical products, excipients of drug products, impurities in drug products, raw materials in drug products, additives to combustible fuels, batched combustible fuels, batched natural occurring products, explosive products, ammunition, gun powder, batched crude oil, batched petroleum distillates, hazardous waste, paper, ink, tire materials, paints and other coatings and other batched manufactured products, including continuously manufactured products or naturally occurring products which are subsequently batched.

In one aspect of the application, there are provided methods for using stable isotope analysis to create isotopic process profiles. As used herein, the term "isotopic process profile" is used to refer to a collection of isotopic data representing distinctive isotopic features or characteristics of a synthesis process used to make a composition. The isotopic process profile in one embodiment is a database of isotopic abundance information corresponding to a given product, the starting materials industrial or pharmaceutical synthesis processes, and possibly intermediates of the process, if intermediates exist and it is desired to include same in the isotopic process profile. Such "isotopic process profiles" can also advantageously include information regarding fractionations corresponding to the synthesis process as a whole, and optionally any sub-reactions thereof.

In accordance with the application, one can assemble an isotopic process profile for a given product, made by a given synthetic pathway, by measuring one or more isotopic features of the starting materials and intermediates of the manufacturing process and retaining records of observed isotopic fractionations ($\Delta$s) of the process, including multi-step syntheses. When both the source of the starting materials and the manufacturing process are held constant (it is understood that "constant" means "within error") during manufacture of a bulk drug substance, similar isotopic ratios are observed in the products. In one embodiment, the measuring of isotopic features includes obtaining an isotopic composition profile for a given material being tested. In another embodiment, the isotopic composition profile includes isotopic abundance data for at least two different isotopes. In yet another embodiment, the isotopic composition profile includes isotopic abundance data for at least three isotopes. In still another embodiment, the isotopic composition profile includes isotopic abundance data for at least four isotopes. Also appropriate for inclusion in an isotopic process profile in one embodiment are data regarding the completeness of chemical reactions and/or sub-reactions used to make the product, if one or more reactions are not allowed to proceed to completion in the chosen synthesis pathway.

Such an isotopic process profile can be useful in a number of ways. For example, an isotopic process profile can be used to later determine whether a target sample of undefined origin was made by the same process, provided that a sufficient number of data points for the target sample are available to establish whether the target sample matches the isotopic process profile. This can be useful for a variety of purposes, including, for example, establishing infringement of a process patent. One way to make such a determination when starting materials and/or intermediates are available is by first determining an isotopic composition profile of the known starting materials and/or intermediates and the reaction product. With reference again to the simple reaction A+B→P, the method can be practiced by first creating an isotopic composition profile for select isotopes for the reactant A, creating a second isotopic composition profile for select isotopes of reactant B and creating a third isotopic composition profile for the product P that includes information for at least one isotope in common with the isotopic composition profile for reactant A and information for at least one isotope in common with the isotopic composition profile for reactant B. Given that the reaction pathway Z by which product P is made from reactants A and B can be characterized using the following four variables: (1) the number of atoms in the reactants (i.e. the stoichiometry, n), (2) the isotopic composition, or isotopic abundance, of select isotopes in those reactants ($\delta$), (3) the fraction of reactants remaining after the reaction (i.e. the conversion of the reactants to products or a measure of progress of the reaction, f), and (4) a measure of the isotopic fractionation of the reaction steps or a magnitude of the isotopic effect ($\epsilon$); information regarding the process can be derived from the relationships of isotope abundances between the starting materials and the product. Specifically, a reaction that occurs under the same conditions and that consumes the same fraction of the starting materials will produce products having predictable ratios of isotopes.

Even if values are not known for all of the identified variables, information regarding the reaction pathway can still be determined by partial knowledge of this information. For example, for the simple reaction A+B→P, assuming a yield of 85% (i.e. f=1-0.85 or f=0.15) is achieved, one might determine that for a given isotopic composition of B ($\delta_B$) the isotopic composition of the product P is 5‰ depleted in the isotope of interest relative to the reactant A. By the method described herein, a product P manufactured by reacting A and B together may be said to be manufactured by the same pathway Z if the reactants A and B are the same and the product P is found to be 5‰ depleted in the isotope of interest relative to the reactant A. If, on the other hand, the reactants A and B are found to be the same and product P is found to be 3‰ enriched relative to the reactant A in the isotope of interest, on cannot conclude that the reaction P was formulated by the same pathway Z. While a large divergence such as the above can lead to a conclusion that a different reaction pathway was employed, it is to be understood that a small difference can result from other factors even if the same pathway is employed. For example, as discussed above, halting the reaction at a different stage short of complete conversion of the reactants can result in products having different isotopic composition profiles.

The records of the four variables as to each pathway can also be utilized to back calculate from the isotopic depletion of product P under a known pathway to determine the isotopic composition of the starting reactant A. With knowledge of how product P is depleted in the isotope of interest in a given synthesis process relative to reactant A, the isotopic composition of the reactant A can be determined. If the isotope of interest in product P is depleted in the course of a certain synthesis process relative to the reactant B, the isotopic concentration of the reactant B can be determined.

Alternatively, the pedigree can be used to build a record for use in manufacturing process control, which can improve manufacturing quality and efficiency, and also provide a useful tool for establishing that manufacturing processes meet regulatory requirements. Once these variables are measured, as long as the process remains the same, the same isotopic relationships should continue to be observed during the use of that synthetic pathway. So, in the manufacturing context, the monitoring of the isotopic compositions of the reactant, intermediates, and products will give a quantitative characterization of whether a process is proceeding within acceptable parameters. One can then monitor quality control by measuring the isotopic compositions of a plurality of components in the pathway and determining whether they are within specified limits. Measurements outside the specified limits would indicate that some aspect of the process has changed such as, for example, reaction time, temperatures, pressure or catalyst activity.

An isotopic process profile can be made in accordance with the application either by performing analyses of starting materials, products, and/or intermediates off-line at an analytical facility separate from the manufacturing location, or by at-line isotopic analysis using process analytical chemistry techniques at the manufacturing location. At-line isotopic measurements can readily be performed on samples removed from the reaction stream as discussed further below.

In addition to the creation of isotopic process profiles, measuring isotopic content of reaction starting materials, intermediates and products periodically, for example, after an isotopic process profile associated with a given synthesis process exists, provides a manner for quantitatively indexing the consistency of the synthesis process. Furthermore, by obtaining the isotopic composition profile of a product and documentation of its synthetic pathways, the details of the synthetic pathway of the products can be accessed via subsequently-measured batch-specific isotopic composition of products from either the supply chain or from the marketplace.

Isotopic analysis can be used to track over time the isotopic fractionation that occurs in synthetic pharmaceutical manufacturing processes. With control of the major variables (i.e., the raw materials and synthetic pathways) that determine the isotopic composition of pharmaceutical materials, the isotopic composition of pharmaceutical products can be predicted as described herein and synthetic processes plausibly monitored. This finds useful application in the R&D laboratory, as well as in pharmaceutical manufacturing and authentication. Thus, isotopic process profiles containing corresponding reaction and/or sub-reaction synthetic isotope fractionation data can advantageously be used for quantitative process monitoring. The isotopic process profile can also integrate specific reaction variables that contribute to the isotopic composition of the synthetic product. In a given process for which the isotopic compositions of the reactants are known and the synthetic isotopic fractionation has previously been determined, the isotopic composition of the product has a predictable isotopic value. If the observed value is not within a predicted range, then some aspect of the synthetic process has varied, such as, for example, the reaction rate as modulated by factors such as pressure, temperature, catalyst activity or reagent abundance. The detection of this variation can operate to actuate a warning signal, bringing to the attention of an operator the possible need for further analysis of the process or corrective action.

Thus, in another aspect of the application, there is provided an analytical tool that is a practical, cost-effective way to analyze and control pharmaceutical manufacturing processes. Given the reproducibility of isotopic ratios in products that are produced using the same batch of starting materials and the same synthesis reactions, the application provides a means by which to monitor the consistency of the synthetic processes, i.e., of either partial or total synthetic pathways. As such, the present application provides a new tool in the field of Process Analytical Chemistry (PAC), which includes taking isotopic abundance measurements for the purpose of control of large-scale chemical processes. In particularly preferred embodiments, the PAC control system includes automatic or semi-automatic sampling systems, mass spectrometer analyzers, and data collecting computer processors.

Advanced data collection and control systems can be configured in accordance with the principles described herein to provide real-time analysis of reaction starting materials, intermediates and products. While PAC systems contemplated by the application preferably include analytical instrumentation on-site for generating isotopic composition profiles, it is important to recognize that the quantification of stable isotopes is necessarily an "off-line" or "extractive" analytical tool because technology does not currently exist that enables one to determine the isotopic composition profile of a composition using remote imaging techniques or by placing a sensing probe into contact with a process stream, which are referred to as "in-line" or "in situ" tools. Rather, it is necessary to use sampling techniques to withdraw a sample from the process flow path, prepare the sample and pass it through a mass spectrometer (analyzer) to obtain the isotope concentration or ratio data. It is therefore important to carefully consider and select a sampling technique to ensure that the sample extracted is representative of the desired material, or the portion of the process, to be tested as a whole.

The application also contemplates a feed-back loop effective to actuate one or more adjustment mechanism that adjusts one or more process parameters (i.e., reaction-rate conditions such as temperature, pressure, rate of reagent inflow, and the like) if warranted as a result of sensed fluctuations in isotope data. For example, future collection of isotopic process profile data associated with a given synthesis process may inform an operator that a fluctuation in isotope ratios of a certain type and magnitude correlates to an identified process parameter. In this case, a feedback loop in the control system can be configured to automatically adjust the identified process parameter upon detection of the fluctuation. Alternatively, the control system can be programmed to simply actuate an alarm when an isotopic ratio outside a predetermined range is detected. In this manner, quantitative chemical information regarding chemical systems can be provided analytically using such a system. The use of a sensing and feedback system in a chemical synthesis process as described herein enables the improvement of modeling and control of chemical processes, resulting in improved quality control, and perhaps improved yield and energy efficiency. In one version, the system is configured such that sample extraction from process flow streams, sample preparation, measurement, data acquisition and interpretation of the analytical results are carried out periodically and automatically under computer control.

Another use of stable isotope analysis methods in accordance with the application relates to the investigation of a suspect sample of undefined origin, for example, in cases such as drug counterfeiting investigations and process patent infringement investigation. These uses can be considered different aspects of what is referred to herein as "pharmaceutical authentication or security." Of course, analogous investigations might be warranted with regard to non-pharmaceutical products and patents as well. Manufacturers and regulatory authorities are confronting pharmaceutical security using multiple diverse tools, which can be categorized as overt techniques, covert techniques or forensic (analytical) techniques, the latter of which has only recently begun to receive significant attention. Purposeful misidentification of pharmaceutical materials threatens the efficacy of end-products and intermediates, consumer confidence, and the economic well-being of pharmaceutical manufacturers. Thus, pharmaceutical manufacturers and regulatory agencies have a strong interest in ensuring product authenticity and security. The main areas of concern associated with purposeful misidentification are counterfeiting, diversion (also known as countertrading), vicarious liability, theft, and patent infringement. With this need in mind, another manner in which the application finds advantageous use is to correlate a sample product (whether of known or unknown origin) to a manufacturing process. In addition to being useful as a pharmaceutical security tool, this aspect of the application also finds advantageous use in establishing that a given product was made using a synthesis process that has been accepted and/or authorized by a regulatory body such as, for example, the FDA.

The present application provides a powerful forensic tool to extract valuable information regarding the synthetic process by which a product of undefined origin was synthesized by analyzing the amounts and/or ratios of natural stable isotopes in a suspect product. In order to inferentially determine whether the product was made using a known synthesis process, it is also necessary to determine, or at least make assumptions, regarding the starting materials used to make the product. The isotopic composition of starting materials, intermediates, and final products can be directly measured if adequate samples are available. For example, in the case of an API, it is often the case that sample starting materials and/or information regarding the starting materials will be available in the records kept by the pharmaceutical company that made the product. Even if actual samples of the starting materials are not available, it is possible that the vendor from which the starting material was obtained might have samples from the same batch or a similar batch of the reagent that can be made available for testing.

With knowledge of the isotopic compositions of the starting materials, and knowledge of isotopic fractionations that can be expected from the synthesis process under review, the isotopic compositions of the resulting chemical products can be predicted. Armed with this information, and the isotopic composition profile of the suspect product, inferences can be accurately drawn regarding whether the suspect product was made using the synthesis process under consideration.

It is also useful to keep in mind that, even if exact isotopic composition profiles cannot be obtained for starting materials used to make a given suspect product, certain assumptions can be made regarding the starting materials that will still enable one to draw inferences regarding the synthesis process used to make the suspect product. For example, because H and O can be presumed to derive largely from meteoric water, assumptions can be made regarding the isotopic ratios thereof in the starting materials. By way of background, the $\delta D$ and $\delta^{18}O$ of surface meteoric water is very highly correlated, spanning about 350‰ in $\delta D$ and about 35‰ in $\delta^{18}O$. This excellent correlation exists in nature because of a process known as Rayleigh fractionation (or, isotopic distillation) of surface water as it is continuously evaporated and condensed in its general equator-to-poles' migration, thereby fractionally distilling the light- from heavy isotopes of water. Thus, even in situations were the starting materials are not available for testing, knowledge of the geographic origin thereof can provide information with which inferences can be drawn using the tools described herein. Similarly with respect to carbon isotope ratios, carbon sources can be, for example, terrestrial C3 photosynthetic organic carbon derived from C3 photosynthetic terrigenous plants, terrestrial C4 photosynthetic organic carbon derived from C4 photosynthetic terrigenous plants, or from marine plants (i.e., algae), each of which is known to have statistically different carbon isotope ratios. Thus, even if samples of starting materials are unavailable for testing, inferences can be drawn from knowledge regarding the derivation or manufacture of the starting materials.

Reference will now be made to the following Examples, which describe experimental work directed to subject matter described herein. It is understood that no limitation to the scope of the application is intended thereby. The Examples are provided solely to promote a full understanding of the concepts embodied in the application.

EXAMPLE ONE

Experimental

To fully elucidate the isotopic fractionations that occur between reaction steps, it is ideal to have at least 0.1 mg of all intermediates and products for each stable isotope ratio being measured.

Carbon and Nitrogen Isotope Analyses.

For analyses of $^{13}C$ and $^{15}N$ ratios, ~0.1 mg solid samples were weighed and placed into tin cups that were crimped tightly closed. The analytical system used was an EA/IRMS, and consisted of a Carlo Erba 1108 Elemental Analyzer, a Conflo II interface, and a Finnigan MAT Delta Plus XL isotope ratio mass spectrometer. The oxidation furnace of the EA was operated at 1020° C., the reduction furnace temperature was at 650° C., and the chromatographic column was heated at 60° C. Isotope ratios are reported in terms of $\delta^{13}C$ values relative to the international VPDB standard and $\delta^{15}N$ values relative to the international AIR standard. The $\delta$ notation is explained in a following section.

Sulfur Isotope Analyses.

Individual solid samples of 0.08-0.10 mg were mixed with 0.5 mg $V_2O_5$ and weighed into tin cups and sealed. Analysis was accomplished using, a second EA/IRMS, that was comprised of a Eurovector Elemental Analyzer Model 3000r, a Micromass Dilutor® interface, and a Micromass Isoprime Isotope Ratio Mass Spectrometer. The oxidation furnace of the EA was operated at 1030° C. The gas flows were 10 ml $O_2$/min and 150 ml He/min. Isotope ratios are reported in terms of $\delta^{34}S$ values relative to the international Canyon Diablo troilite standard (CDT).

Hydrogen and Oxygen Isotope Analyses.

Prior to analysis, solid samples were equilibrated for several days at ambient temperature with water vapor by exposure to the laboratory atmosphere in order to fully exchange labile H/D sites and any water present in hydrated form. (e.g., Refs. 6-9). Following equilibration, ~0.2 mg samples were weighed into silver boats which were then crimped tightly. For solid samples, a Finnigan Thermal Conversion/Elemental Analyzer (TCEA) interfaced to a Finnigan Delta Plus XL isotope-ratio mass spectrometer (TCEA/IRMS) was employed. The same system was used for liquid samples but a direct liquid-injection port was fitted in place of the autosampler. The TCEA pyrolyzes the samples at 1350° C. to quantitatively generate $H_2$ and CO which are subsequently chromatographically separated at 85° C. Isotope ratios are reported in terms of $\delta D$ values and $\delta^{18}O$ values relative to the international VSMOW standard.

Terminology for Isotopic Relationships Between Precursors and Products

Isotopic calculations are based on only two systems of equations. The first employs mass balances and the second involves integrated forms of rate equations that pertain only to kinetically controlled isotopic fractionations. Equations describing mass balances are exact when cast in terms of fractional abundances [e.g., $^{13}C/(^{12}C+^{13}C)$]. In contrast, assessments of differential rates are based on isotope ratios (e.g., $^{13}C/^{12}C$). When these systems must be blended, either approximations or equations with multiple terms are employed. For details, see Hayes (10).

The relevant isotopic parameters are stoichiometry (n), isotopic abundance ($\delta$) the magnitude of the isotopic effect ($\epsilon$) and a variable related to conversion of reactants to products (f).

n represents the stoichiometry of the reaction, more specifically the number of atoms of a given element (e.g., carbon) in a given molecule involved in the reaction.

$\delta$ A measure of isotopic abundance, $\delta$, is usually reported as the difference in parts per thousand, or permil (‰), from an international standard. $\delta$ can be negative or positive depending on whether the sample is enriched or depleted in the heavy isotope relative to the standard. For example, in the case of carbon the difference is calculated as $$\delta^{13}C\ (‰)=([(R_{smpl})/(R_{std})]-1)\cdot(1000) \qquad (15)$$

where $R_{smple}$ is the $^{13}C/^{12}C$ ratio of the sample and $R_{std}$ is the $^{13}C/^{12}C$ ratio in the standard. $\delta$ is thus linearly proportional to the isotopic ratio in the sample. Standards are available from the International Atomic Energy Authority and a standard for each isotope is used to determine the zero point of an abundance scale for that isotope. Standards include average seawater for H and O, calcium carbonate for C, air for N, and a meteorite for S. When the sample is depleted in the heavy isotope relative to the standard, $\delta$ is negative and when the sample is enriched it has a positive value. If it has the same isotopic abundance then $\delta=0$ (cf. Ref. 11).

$\epsilon$ is a measure of the magnitude of an isotope effect. Its value depends on details of the reaction and on the relative mass difference between isotopes. Effects are largest for D vs. H and smaller for heavier elements. In general, the values of $\epsilon$ are specific to individual positions within the molecules involved. They are largest at the reaction site, much smaller at neighboring positions, and usually not measurable elsewhere. Like $\delta$, $\epsilon$ relates to the isotopic difference between two materials (e.g., reactant and product) and is usually expressed in permil. For kinetic isotope effects, in the system employed here, $\epsilon=-10‰$ means that a reaction site bearing the heavy isotope reacts 10 parts per thousand, or 1%, more slowly than a site bearing a light isotope. For equilibrium isotope effects, $\epsilon_{A/B}=15‰$ would mean that, at equilibrium, A was enriched in the heavy isotope by 15 parts per thousand relative to B. Here, A and B refer to specific atomic positions that can be related by a chemical equilibrium.

f is a measure of the progress of a reaction. It is the most important variable governing fractionations caused by isotope effects. Its value ranges from 1 to 0 and depends on factors such as temperature, pressure, or availability of reactants. In equilibria (A⇌B), f indicates the position of the equilibrium, with $f_B=1$ indicating complete conversion to B and, at any position, $f_A+f_B=1$. In irreversible reactions, $f_X$ indicates the portion of reactant X which remains unconsumed, with $f_X \rightarrow 0$ as the reaction proceeds to completion.

The precision of isotopic analyses is typically calculated by two methods. Pooled standard deviations of raw data are typically computed from sets of duplicate or triplicate measurements (13). From those pooled standard deviations, standard deviations of mean values pertaining to specific substances are calculated. More specifically, the standard deviation of a mean value is the pooled standard deviation divided by $n^{1/2}$, where n is the number of measurements performed on a given sample (13). For carbon, nitrogen, oxygen, and sulfur, the resulting 95% confidence intervals for a result are typically in the range of ±0.1- to ±0.4‰. For hydrogen, the 95% confidence interval is typically ±3‰.

Discussion

Precise quantitation of stable isotopic compositions in pharmaceutical intermediates and products requires both mass balance and isotopic fractionation equations that are applicable to both single and multi-step reaction sequences. We start from the most basic requirement of mass balance then consider isotopic fractionations in a single reaction. Finally, we discuss applications to the protection of process patents.

Mass Balance

For A+B→P, where reactants A and B are quantitatively converted to product P, two mass balances can be written:

$$m_A + m_B = m_P \tag{16}$$

$$m_A \delta_A + m_B \delta_B = m_P \delta_P \tag{17}$$

where, $m_A$, $m_B$, and $m_P$ are molar amounts of carbon (or any other element) in A, B, and P and the isotopic compositions of that carbon (or any other element) in A, B, and P are given by $\delta_A$, $\delta_B$, and $\delta_P$. Equation 1 is a mass balance (i.e., carbon in = carbon out) while equation 2 is an isotopic mass balance ($^{13}$C in=$^{13}$C out). Under the conditions postulated (quantitative conversion) the isotopic composition of P can be computed from those of A and B (10, 11).

Isotopic Fractionation

Figure 4:
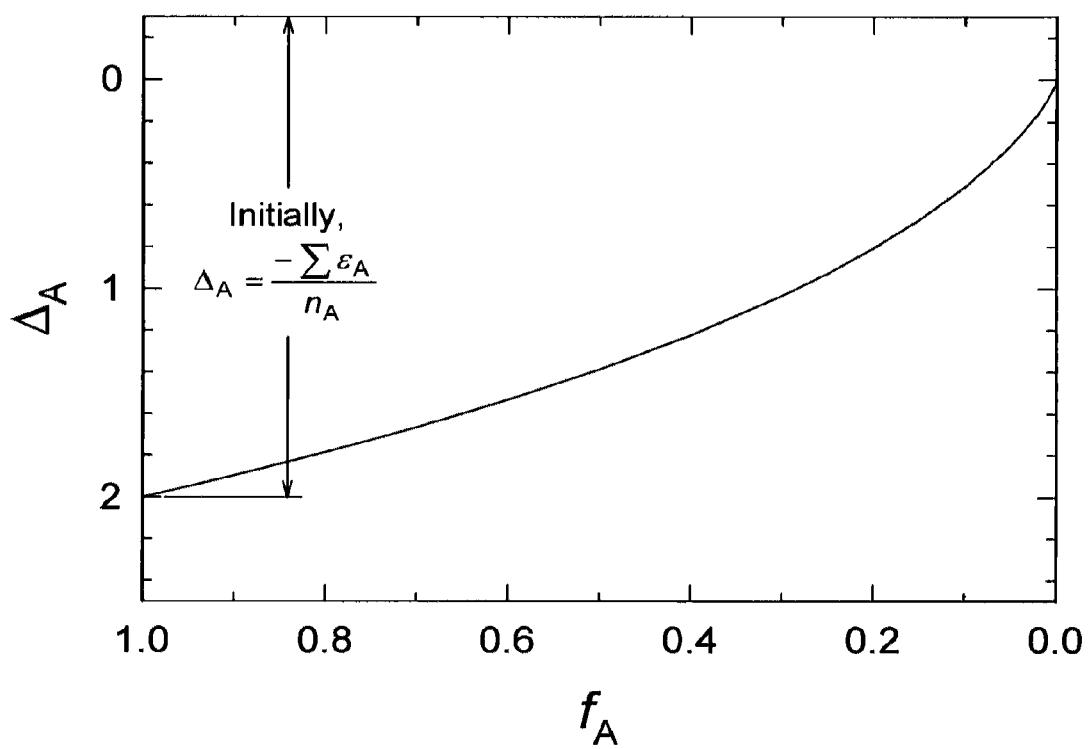
FIG. 4 depicts $\Delta_A$ as a function of $f_A$, the fraction of A remaining unconsumed. As shown in equation 3, $\Delta_A$ quantifies the extent to which atoms derived from reactant A and incorporated in the product are depleted in the heavy isotope. The line shown here was calculated using the exact form of the equation relating f and the isotopic composition of a product (14). To provide a quantitative example, the sum of the isotope effects at all positions in A ($= \Sigma \epsilon_A$) was assumed to be 10‰ and the reactant was assumed to contain 5 atoms of the fractionated element. At the outset of the reaction ($f_A = 1$), the depletion amounts to $\Sigma \epsilon / n = 10/5 = 2$‰. If A is consumed quantitatively ($f_A = 0$), there is no fractionation ($\Delta_A = 0$).

For isotopic fractionations, calculations must take into account factors such as reaction completeness and isotope effects. These will cause the isotopic composition of P to differ from that computed using the mass balance equation and assuming quantitative conversion of reactants to products. To provide a concrete example, assume that A is present in excess while B, the limiting reactant, is quantitatively converted to product. In that case $$n_A(\delta_A - \Delta_A) + n_B \delta_B = n_P \delta_P \tag{18}$$

where $n_A$, $n_B$, and $n_P$ represent the numbers of atoms of carbon (or any other element of interest) in A, B, and P. Because A is not quantitatively converted to product, the isotopic compositions of the A-derived positions in P can differ from those in the initial reactant. Here, that isotopic offset is expressed as $\Delta_A$. As shown in FIG. 4, its value depends on the isotope effect(s) and on the fraction of A that remains unconsumed. If the reaction conditions, particularly the magnitude of the excess of A, are consistent, $\Delta_A$ will be constant. Because the n values are known exactly, $\Delta_A$ can be determined from equation 18 after isotopic analysis of the reactants and product (i.e., determination of $\delta_A$, $\delta_B$, and $\delta_P$).

Values of $\delta_A$, $\delta_B$, and $\delta_P$ do not affect the values of $\Delta_A$. Accordingly, once $\Delta_A$ is known for a given reaction and set of conditions, it is necessary only to know two of the δ values in order to compute the third. Thus, for example, when $\Delta_A$, $\delta_A$, and $\delta_B$, are known, the isotopic value of the product ($\delta_P$) can be calculated.

If neither A nor B is completely consumed during the course of the reaction, and if the rate of the chemical reaction (or position of the chemical equilibrium) is sensitive to isotopic substitution on both reactants, it will be necessary to consider values of both $\Delta_A$ and $\Delta_B$:

$$n_A(\delta_A - \Delta_A) + n_B(\delta_B - \Delta_B) = n_P \delta_P \tag{19}$$

If reaction conditions cannot be manipulated so that $f_A$ and $f_B$ (and thus $\Delta_A$ and $\Delta_B$) can be independently driven to completion (i.e., zero), it will be possible to determine only the sum, $n_A \Delta_A + n_B \Delta_B$. From theoretical considerations (14), $\Delta_A$ and $\Delta_B$ can be evaluated separately for all values of $f_A$ and $f_B$ if the isotope effects are known.

EXAMPLE TWO

Isotopic fractionations like those discussed above accumulate during the different steps of a multi-step synthesis scheme. They can, however, be individually and systematically differentiated, not only for multiple reactants but also for multiple isotopes. To provide an example consider carbon-isotopic fractionations in a hypothetical four-step sequence:

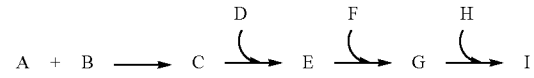

Figure 5:
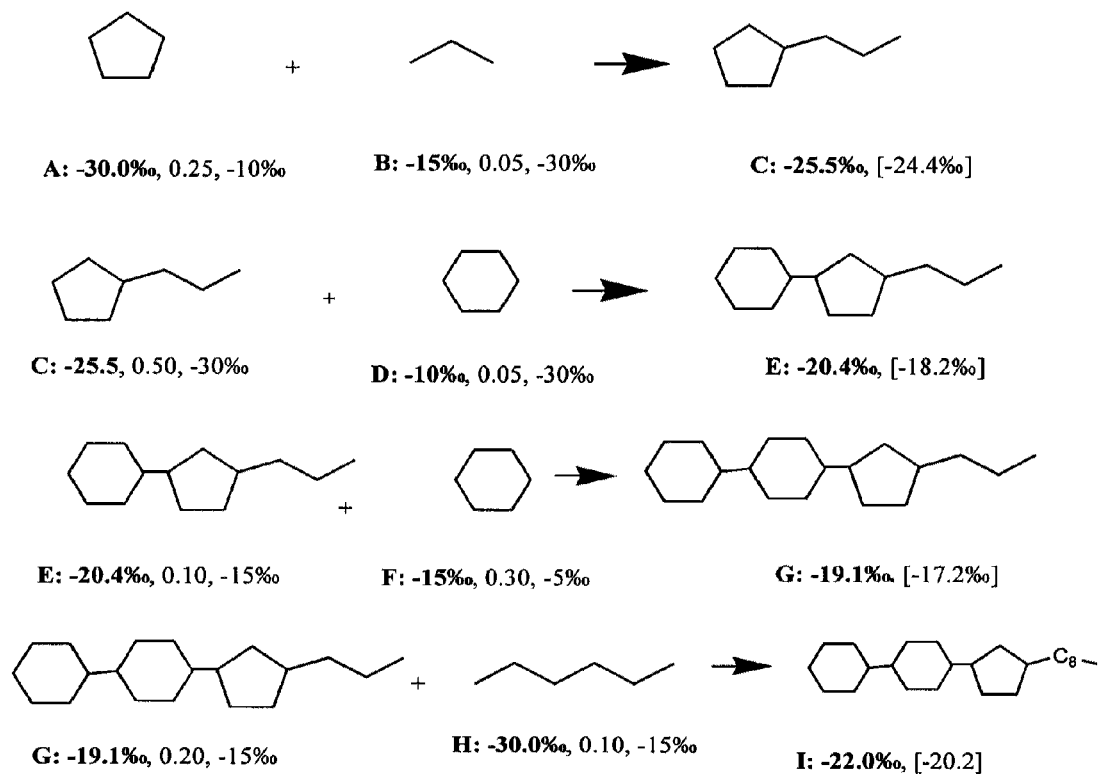
FIG. 5 illustrates the effects of the four key isotopic variables (n, δ, f, ε) on the isotopic compositions of the three synthetic intermediates (C, E, G) and of the final product, I ($\delta_P$). For all eight reactants (left), the given numerical values are δ, f, and ε. For all four products (right), the numerical values are the isotopic compositions actually observed ($\delta_P$) and that expected in the absence of isotope effects and incomplete consumption of reactants ([$\delta_P^*$]).

Illustrative carbon skeletons for reactants and products are shown in FIG. 5 with pertinent quantities summarized in Table 2.

TABLE 2

Properties of Four-Step Synthetic Sequence[a]

| Reactants | | | | | | Conditions | | | | Product | |
|---|---|---|---|---|---|---|---|---|---|---|---|
| 1 | 2 | $n_1$ | $n_2$ | $\delta_1$, ‰ | $\delta_2$, ‰ | $f_1$ | $f_2$ | $\Sigma\epsilon_1$, ‰ | $\Sigma\epsilon_2$, ‰ | | $\delta_P^*$, ‰ | $\delta_P$, ‰ |
| A | B | 5 | 3 | −30.0 | −15.0 | 0.25 | 0.05 | −10.0 | −30.0 C | −24.4 | −25.5 |
| C | D | 8 | 6 | −25.5 | −10.0 | 0.50 | 0.05 | −30.0 | −5.0 E | −18.2 | −20.4 |
| E | F | 14 | 6 | −20.4 | −15.0 | 0.10 | 0.30 | −15.0 | −5.0 G | −17.2 | −19.1 |
| G | H | 20 | 6 | −19.1 | −30.0 | 0.20 | 0.10 | −15.0 | −15.0 I | −20.2 | −22.0 |

[a]The sequence of reactants and products is given by equations 5-8 in the text. The numbers of carbon atoms and the carbon-isotopic compositions of reactants 1 and 2 in each step are given by $n_1$, $n_2$, $\delta_1$, and $\delta_2$. The fractions of each reactant unconsumed in each step are given by $f_1$ and $f_2$. The sums of all carbon isotope effects pertaining to each reactant are given by $\Sigma\epsilon_1$ and $\Sigma\epsilon_2$. The isotopic compositions that successive products would have in the absence of isotope effects are given by $\delta_P^*$ and the isotopic compositions actually observed are given by $\delta_P$.

The carbon numbers ($n_1$, $n_2$), initial isotopic compositions ($\delta_1$, $\delta_2$), fractions of reactants remaining unconsumed ($f_1$, $f_2$) and summed isotope effects ($\Sigma\epsilon_1$, $\Delta\epsilon_2$) were chosen to be representative of a typical synthetic scheme. All isotope effects were assumed to be kinetic. Values of $\delta_P{}^*$, the isotopic compositions that would be observed if isotopic fractionations were absent, were calculated using equation 4 with $\Delta_A = \Delta_B = 0$; that is, the simple mass balance equations 16 and 17. Values of $\delta_P$, the isotopic compositions that would actually be observed for the successive products, were calculated using exact forms of integrated rate equations (14).

Figure 6A:
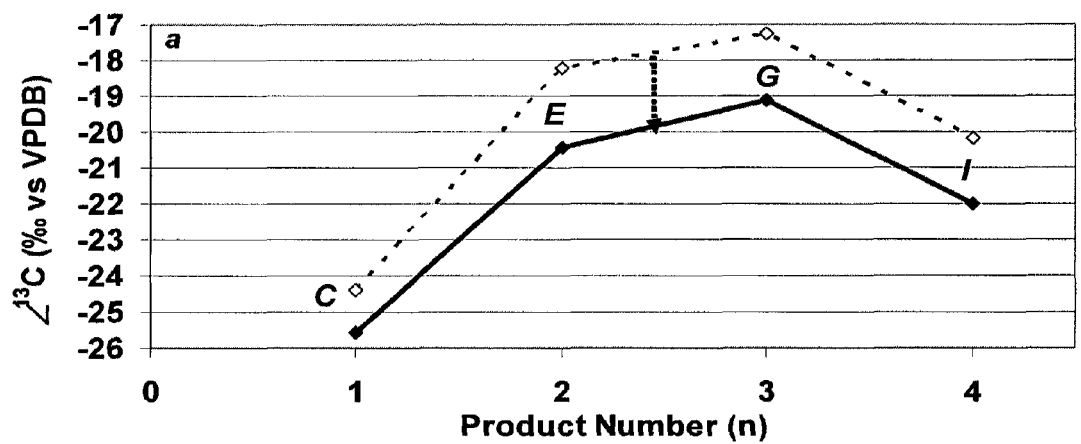
FIG. 6. (a) The carbon-isotopic composition ($\delta^{13}C$) of synthetic intermediates (C, E, G) and the final product, I, as a function of reaction step with (upper line) and without (lower line) the contributions of partial-reaction completion (f) and isotopic fractionation (ε).
Figure 6B:
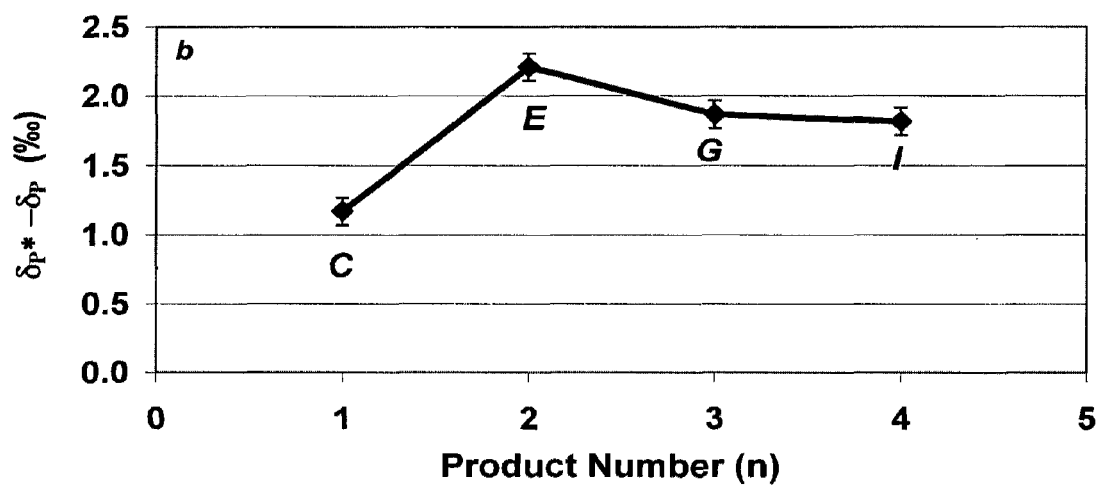

This example illustrates the interplay of the four factors that control the isotopic compositions of manufactured products, namely the stoichiometries and isotopic compositions of the starting materials, isotope effects associated with the synthetic reactions, and the degree to which conversions of precursors to products are quantitative. The isotopic compositions of all products are dominated by the initial isotopic abundance of the precursor materials and are variously modulated (viz., depleted) by the degree of completion (f) and the magnitude of any isotopic effects ($\epsilon$, FIG. 6a). A plot that summarizes the difference between the isotopic compositions that are predicted and those that would be observed in the absence of isotope effects ($\delta_P{}^* - \delta_P$) is shown in FIG. 6b. These values are also shown in the last two columns of Table 2. In the first synthetic step, isotope effects on reactant B are rather large, but that reactant is consumed almost completely. The resulting isotopic fractionation is less than 1‰ (the larger value shown in FIG. 6b pertains to the product and reflects fractions affecting both reactants). In the second step, a large isotope effect and poor conversion of reactant C lead to a large isotopic fractionation at the reaction site. However, fractionation is diluted now that the product contains 14 carbon atoms. As shown in FIG. 6b, the overall difference between real and hypothetical unfractionated products is barely doubled. In the remaining steps, where isotope effects are moderate and consumption of reactants is relatively efficient isotopic fractionation declines.

EXAMPLE THREE

Applications in the Pharmaceutical Industry

Measuring and tracking isotopic fractionations in synthetic pathways used to prepare pharmaceutical products has potential uses in Process Analytical Chemistry (PAC) and for protection of process patents. In Process Analytical Chemistry, the matrix of information obtainable provides a complete isotopic description of pharmaceutical materials from starting materials through synthetic intermediates to final products. Starting materials reacted under consistent conditions with isotopically controlled reagents should always produce products of known isotopic composition. Divergences from the predicted isotopic pathways suggest uncontrolled variables in pharmaceutical manufacture and provide insight into process consistency. When the goal of PAC is understanding manufacturing processes, the complete stable-isotopic record of synthesis summarizes many of the key process variables: reaction rate as affected by the synthetic pathway, reaction rates, temperature, pressure, compound concentration, etc.

The general concepts of the complete isotopic description of a hypothetical reaction shown in FIG. 6 can be used to monitor synthetic processes. Each step of a reaction starts with precursors of known stoichiometric composition (n) and measurable isotopic composition ($\delta$). Reactions proceeding to a large degree of completeness (f) and isotopic fractionation ($\epsilon$) yield a product whose isotopic composition ($\delta_P$) can be measured and predicted. The sum of this information (n, $\delta$, f, $\epsilon$) is a very specific isotopic description of both individual reactions and multi-step sequences (e.g., Table 2). While the sensitivity of isotopic compositions to key reaction variables—or even specific variables—would require calibration like all PAC variables, it should be imminently achievable. Thus, manufacturing records of isotopic variables (n, $\delta$, f, $\epsilon$) would contain an isotopic record of the synthetic pathway employed.

Understanding isotopic process parameters can be useful in process-patent protection applications. With a full description of a given pharmaceutical synthetic pathway, the isotopic differences between any precursor and another precursor or a precursor and the final product can in principle be predicted or at least provisionally understood. This provides valuable insight into which synthesis process was used and consistencies in expected isotopic matrix values can provide important information about process counterfeiting

Summary

Stable isotopic fractionations resulting from isotope effects are usually large in comparison to the precision of isotopic measurements. These fractionations significantly modulate the isotopic compositions that would be observed if isotopic compositions of starting materials were the only controlling factor. The fractionations depend not only on the magnitudes of isotope effects associated with the synthetic reactions employed, but also on reaction conditions, specifically those affecting the extent to which reactants are converted to products. Because of these phenomena, the final isotopic composition of a manufactured product is directly related to the synthetic scheme used. Subsequently, PAC using stable-isotopic analysis can be useful not only for product authentication but also for process monitoring or reconstructing the processes by which the product was synthesized.

REFERENCES

1. Jasper J P. *Tablets and Capsules,* 2004; 2(3):37.
2. Jasper J P, Lyon R C, and Weaner L E. *Pharm. Mfg.,* 2005; 4(5):28.
3. Jasper J P, Fourel F, Eaton A, Morrison J, and Phillips A. *Pharm. Technol.,* 2004; 28(8):60.
4. Jasper J P, Westenberger B J, Spencer J A, Buhse L F, and Nasr M. *J. Pharm. Biomed. Anal.;* 2004; 35:21.
5. Wokovich A M, Spencer J A, Westenberger B J, Buhse L F, and Jasper J P. *J. Pharm. Biomed. Anal.,* 2005; 38:781.
6. Schimmelman A, Lewan, M D, and Wintsch R P. 63(22), 1999:3751-3766.
7. Wassenaar L I, and Hobson K A. Environ. Sci. Technol., 2000; 34:2354-2360.
8. Sauer P E, Eglinton T I, Hayes J M, Schimmelman A, and Sessions A L. *Geochim. Comsochim. Acta,* (2001) 65(2): 213-222.
9. Chikaraishi Y, Naraoka H. *Phytochem.,* 2003; 63:361-371.
10. Hayes J M., 2004; http://www.nosams.whoi.edu/docs/IsoCalcs.pdf
11. Jasper, J P. *Pharm. Tech.,* 1999; 23(10):106-114.
12. Hayes J M, 2002; http://www.nosams.whoi.edu/docs/IsoNotesAug02.pdf
13. Jasper J P. *Rap. Comm. Mass Spec.,* 2001; 15:1554.
14. Scott K M, Lu X, Cavanaugh C M, and Liu J S. *Geochim. Cosmochim. Acta,* 2004; 68(3):433.

As will be appreciated by a person of ordinary skill in the art upon consideration of the detailed descriptions herein, the present application has many aspects and embodiments. In one aspect, the application provides a method for constructing an isotopic process profile for a first product made using a known synthetic process that includes (1) obtaining an isotopic composition profile for the first product and for one or more starting material used to make the first product; (2) determining isotopic fractionation values for one or more reaction steps in the known synthetic process; and (3) providing a database that includes a plurality of data selected from the group consisting of (i) the isotopic composition profile for the first product, (ii) the isotopic composition profile for one or more starting material used to make the first product, and (iii) isotopic fractionation values for one or more reaction steps in the known synthetic process; wherein the database is an isotopic process profile of the product.

In another aspect of the application, there is provided a method for using the isotopic process profile that includes (1) identifying a second product of undefined origin; (2) obtaining an isotopic composition profile for the second product; (3) determining within an acceptable error whether the second product was made using the known synthetic process by comparing the isotopic composition profile for the second product to the isotopic process profile.

In yet another aspect, the application provides a method for determining whether a product of undefined origin was made by a first known synthetic process. The method includes (1) obtaining a first isotopic composition profile for the product; (2) providing fractionation information regarding the first known synthetic process, the starting materials used to make the product, or both; and (3) inferentially determining whether the compound was made by the first known synthetic process by comparing the first isotopic composition profile to the information.

The application provides in still another aspect a method for monitoring process quality of a chemical synthesis process. The method includes (1) defining an acceptable range of isotopic abundance at an intermediate point in the chemical synthesis process for at least one stable isotope, the acceptable range encompassing isotopic abundance values that exist when the process is proceeding in an acceptable manner; (2) periodically extracting samples from the chemical synthesis process at the intermediate point; (3) measuring the actual isotopic abundance for the at least one stable isotope in the samples; and (4) comparing the actual isotopic abundance to the acceptable range to determine whether the chemical synthesis process is proceeding in an acceptable manner.

The application also provides a system for monitoring process quality of a chemical synthesis process that includes (1) a sample extraction device operable to periodically obtain samples from a process stream for the chemical synthesis process at an intermediate point in the process; (2) a measuring instrument operable to receive the samples from the extraction device and determine actual isotopic abundance information for one or more isotopes in the samples; and (3) a computer processor operable to store and display the isotopic abundance information. In one embodiment, the system also includes a feedback loop operably connected to the computer processor to adjust process parameters in the chemical synthesis process using defined routines if the actual isotopic abundance information is outside acceptable ranges.

In another aspect of the application there is provided a method for making a new product batch that has a unique isotopic composition profile different than a previously-made product batch with the same molecular content. The method includes adjusting at least one aspect of the manufacturing process for the product in a manner selected from the group consisting of (i) selecting a starting material having a different isotopic composition profile, (ii) identifying a chemical reaction in the process that has an isotope effect, and halting the reaction at a different stage short of completion, (iii) identifying a chemical reaction in the process that has an isotope effect, and making the limiting reagent one that is not used to derive the isotopic composition profile of the product, (iv) altering the amount of the limiting reagent of (iii) that is available for reaction, and (v) mixing into the product an excipient having a different isotopic composition profile.

The present application contemplates modifications as would occur to those skilled in the art without departing from the spirit of the invention. In addition, the various procedures, techniques, and operations may be altered, rearranged, substituted, deleted, duplicated, or combined as would occur to those skilled in the art. All publications, patents, and patent applications cited in this specification are herein incorporated by reference as if each individual publication, patent, or patent application was specifically and individually indicated to be incorporated by reference and set forth in its entirety herein.

Unless specifically identified to the contrary, all terms used herein are used to include their normal and customary terminology. Further, while the invention has been described in detail in the foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present application and is not intended to limit the present application in any way to such theory, mechanism of operation, proof, or finding. In reading the claims, words such as "a," "an," "at least one" and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A method for constructing an isotopic process profile for a first product made using a known synthetic process, comprising:

obtaining a first isotopic composition profile for the first product and a second isotopic composition profile for one or more starting material used to make the first product;

determining isotopic fractionation values for one or more reaction steps in the known synthetic process; and providing a database that includes a plurality of data selected from the group consisting of (i) the first isotopic composition profile for the first product, (ii) the second isotopic composition profile for one or more starting material used to make the first product, and (iii) isotopic fractionation values for one or more reaction steps in the known synthetic process;

wherein the database is an isotopic process profile of the product.

2. The method in accordance with claim 1 wherein each of the first and second isotopic composition profile comprises a plurality of data points, each data point defined as the concentration of an isotope or the ratio of two stable isotopes of an element analytically determined to be intrinsically present in the product.

3. The method in accordance with claim 2 wherein at least one of the first and second isotopic composition profile comprises concentration or ratio data for a plurality of stable isotopes intrinsically present in the product.

4. The method in accordance with claim 1 wherein the product is selected from the group consisting of a compound, an active pharmaceutical ingredient, an excipient and a bulk drug product.

5. The method in accordance with claim 1, further comprising recording the isotopic process profile in a tangible medium.

6. The method in accordance with claim 5 wherein the tangible medium is a machine readable medium.

7. An isotopic process profile recorded in a tangible medium made in accordance with claim 5.

8. A method for using the isotopic process profile of claim 1, comprising:
    identifying a second product of undefined origin;
    obtaining an isotopic composition profile for the second product;
    determining within an acceptable error whether the second product was made using the known synthetic process by comparing the isotopic composition profile for the second product to the isotopic process profile.

9. The method in accordance with claim 8 wherein said determining further includes comparing the isotopic composition profile for the second product to the isotopic composition profiles for one or more similar products made using other synthetic processes, other starting materials or other synthetic process and other starting materials.

10. The method in accordance with claim 8 wherein said determining further includes making assumptions regarding the potential isotopic abundance values for starting materials used to make the second product.

11. A method for determining whether a product of undefined origin was made by a first known synthetic process, comprising:
    obtaining a first isotopic composition profile for the product;
    providing fractionation information regarding the first known synthetic process, the starting materials used to make the product, or both; and
    inferentially determining whether the product of undefined origin was made by the first known synthetic process by comparing the first isotopic composition profile to the information.

12. The method in accordance with claim 11 wherein the isotopic composition profile comprises a plurality of data points, each data point defined as the concentration of an isotope or the ratio of two isotopes of an element analytically determined to be intrinsically present in the product.

13. The method in accordance with claim 11 wherein the known information comprises information selected from the group consisting of:
    a second isotopic composition profile for one or more of the starting materials used to make the product,
    a third isotopic composition profile for a first comparative sample of product made using the known synthetic process and different starting materials,
    the third isotopic composition profile and a fourth isotopic composition profile for starting materials used to make the compound in the comparative sample, and
    a fifth isotopic composition profile for the starting materials used to make a second comparative sample product and a calculated isotopic composition profile determined to be present in the second comparative sample made using the starting materials and the known synthetic process.

14. The method in accordance with claim 11 wherein the known synthetic process is known only by its fractionation values corresponding to the isotopes evaluated.

15. The method in accordance with claim 11 wherein the known synthetic process is known by the degree of reaction completeness for each starting material and synthetic intermediate of the synthetic process.

16. The method in accordance with claim 11 wherein the known synthetic process is known by the isotopic fractionations associated with each reaction in the synthetic process.

17. The method in accordance with claim 11 wherein the known synthetic process is known by the degree of reaction completeness for each starting material and synthetic intermediate and the isotopic fractionations associated with each reaction in the synthetic process.

18. The method in accordance with claim 11 wherein the first isotopic composition profile has associated therewith a sampling error value based upon its pooled standard error.

19. The method in accordance with claim 11 wherein the first isotopic composition profile includes at least three data points.

20. The method in accordance with claim 11 wherein the first isotopic composition profile includes at least four data points.

21. The method in accordance with claim 11 wherein the first isotopic composition profile includes at least five data points.

22. The method in accordance with claim 11 wherein the first isotopic composition profile includes at least six data points.

23. The method in accordance with claim 11 wherein the first isotopic composition profile includes at least seven data points.

24. The method in accordance with claim 11 wherein the first isotopic composition profile includes at least eight data points.

25. The method in accordance with claim 11 wherein the first isotopic composition profile is provided in machine readable form.

26. The method in accordance with claim 11 wherein the element is a light element.

27. The method in accordance with claim 11 wherein the product is selected from the group consisting of a chemical product, a petroleum sample, a pharmaceutical product, a biomedical sample, a paint sample, an explosive-ammunition sample and a combustible fuel sample.

28. The method in accordance with claim 11 wherein the product is selected from the group consisting of an API, a drug product, an excipient of a drug product and an impurity of a drug product.

29. A method for monitoring process quality of a chemical synthesis process, comprising:
    defining an acceptable range of isotopic abundance at an intermediate point or an end point in the chemical synthesis process for at least one stable isotope, the acceptable range encompassing isotopic abundance values that exist when the process is proceeding in an acceptable manner;
    periodically extracting samples from the chemical synthesis process at the intermediate point or the end point;
    measuring the actual isotopic abundance for the at least one stable isotope in the samples; and comparing the actual isotopic abundance to the acceptable range to determine whether the chemical synthesis process is proceeding in an acceptable manner.

30. The method in accordance with claim 29 wherein said defining comprises defining an acceptable range of isotopic abundance at an intermediate point or an end point in the chemical synthesis process for at least two stable isotopes, the acceptable range encompassing isotopic abundance values that exist when the process is proceeding in an acceptable manner.

31. A system for monitoring process quality of a chemical synthesis process, comprising:
a sample extraction device operable to periodically obtain samples from a process stream for the chemical synthesis process at an intermediate point or an end point in the process;
a measuring instrument operable to receive the samples from the extraction device and determine actual isotopic abundance information for one or more isotopes in the samples; and
a computer processor operable to store and display the isotopic abundance information.

32. The system in accordance with claim 31, further comprising a feedback loop operably connected to the computer processor to adjust process parameters in the chemical synthesis process using defined routines if the actual isotopic abundance information is outside acceptable ranges.

33. A method for making a new product batch that has a unique isotopic composition profile different than a previously-made product batch with the same molecular content, comprising adjusting at least one aspect of the manufacturing process for the product in a manner selected from the group consisting of (i) selecting a starting material having a different isotopic composition profile, (ii) identifying a chemical reaction in the process that has an isotope effect, and halting the reaction at a different stage short of completion, (iii) identifying a chemical reaction in the process that has an isotope effect, and making the limiting reagent one that is not used to derive the isotopic composition profile of the product, (iv) altering the amount of the limiting reagent that is available for reaction, and (v) mixing into the product an excipient having a different isotopic composition profile.

* * * * *